(12) United States Patent
LaVon et al.

(10) Patent No.: US 7,824,386 B2
(45) Date of Patent: Nov. 2, 2010

(54) METHOD FOR USING A DISPOSABLE ABSORBENT ARTICLE AS A SWIM PANT

(75) Inventors: Gary Dean LaVon, Liberty Township, OH (US); Thomas Henrich, Montgomery, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 868 days.

(21) Appl. No.: 11/588,134

(22) Filed: Oct. 26, 2006

(65) Prior Publication Data
US 2008/0103471 A1   May 1, 2008

(51) Int. Cl.
*A61F 13/15* (2006.01)
(52) U.S. Cl. .............. 604/385.14; 604/385.13; 604/385.01; 604/385.03; 604/378; 604/385.101; 604/385.11
(58) Field of Classification Search ............ 604/385.14, 604/385.01, 385.101, 378, 385.11, 385.13, 604/385.03
See application file for complete search history.

(56) References Cited

U.S. PATENT DOCUMENTS

| 833,849 | A | 10/1906 | Schiff |
|---|---|---|---|
| 1,695,109 | A | 12/1928 | Kosloff |
| 1,893,745 | A | 1/1933 | Josias |
| 2,468,445 | A | 4/1949 | Hurst |
| 2,476,585 | A | 7/1949 | Cohen |
| 2,530,647 | A | 11/1950 | Buchler |
| 2,574,279 | A | 11/1951 | Oberle |
| 2,688,328 | A | 9/1954 | Marcus |
| 2,695,025 | A | 11/1954 | Andrews |
| 2,788,786 | A | 4/1957 | Dexter |
| 2,826,199 | A | 3/1958 | Brandon |
| 2,832,346 | A | 4/1958 | Morstad |
| 2,842,129 | A | 7/1958 | Ernstorff |
| 2,868,205 | A | 1/1959 | Epstein |

(Continued)

FOREIGN PATENT DOCUMENTS

CN         2073744 U     3/1991

(Continued)

OTHER PUBLICATIONS

U.S. Appl. No. 11/588,135, filed Oct. 10, 2006, Lavon.

(Continued)

*Primary Examiner*—Jacqueline F. Stephens
(74) *Attorney, Agent, or Firm*—Charles R. Matson

(57) ABSTRACT

Aspects of the present disclosure involve new methods for using disposable absorbent articles having replaceable absorbent core components as a swim pant. Non-removable absorbent core components may be disposed in a chassis of the disposable absorbent article. The absorbent article may also include replaceable absorbent core components adapted to be selectively disposed in capillary liquid communication with the non-removable absorbent core component. Embodiments of such absorbent articles can be configured for use as a swim pant or diaper with relatively low absorbency by removing the replaceable absorbent core component. Removal of the replaceable core component may be done without having to remove the absorbent article from the wearer. In addition, embodiments of the absorbent articles can be reconfigured for use as a high absorbency diaper by reinstalling a replaceable absorbent core component without having to remove the absorbent article from the wearer.

12 Claims, 19 Drawing Sheets

U.S. PATENT DOCUMENTS

| | | |
|---|---|---|
| 3,050,063 A | 8/1962 | Margraf |
| 3,162,196 A | 12/1964 | Salk |
| RE26,151 E | 1/1967 | Duncan et al. |
| 3,306,293 A | 2/1967 | Marder et al. |
| 3,556,932 A | 1/1971 | Coscia et al. |
| 3,595,235 A | 7/1971 | Jespersen |
| 3,658,064 A | 4/1972 | Pociluyko |
| 3,661,875 A | 5/1972 | Sieja |
| 3,771,524 A | 11/1973 | Ralph |
| 3,848,594 A | 11/1974 | Buell |
| 3,860,003 A | 1/1975 | Buell |
| 3,886,941 A | 6/1975 | Duane et al. |
| 3,911,173 A | 10/1975 | Sprague, Jr. |
| 3,918,433 A | 11/1975 | Fuisz |
| 3,926,189 A | 12/1975 | Taylor |
| 4,019,517 A | 4/1977 | Glassman |
| 4,022,210 A | 5/1977 | Glassman |
| 4,062,817 A | 12/1977 | Westerman |
| 4,072,150 A | 2/1978 | Glassman |
| 4,076,663 A | 2/1978 | Masuda et al. |
| 4,081,301 A | 3/1978 | Buell |
| 4,093,776 A | 6/1978 | Aoki et al. |
| 4,257,418 A | 3/1981 | Hessner |
| 4,260,443 A | 4/1981 | Lindsay et al. |
| 4,265,245 A | 5/1981 | Glassman |
| 4,326,302 A | 4/1982 | Lowe et al. |
| 4,467,012 A | 8/1984 | Pedersen et al. |
| 4,496,360 A | 1/1985 | Joffe et al. |
| 4,515,595 A | 5/1985 | Kievit et al. |
| 4,560,381 A | 12/1985 | Southwell |
| 4,573,986 A | 3/1986 | Minetola et al. |
| 4,578,073 A | 3/1986 | Dysart et al. |
| 4,597,760 A | 7/1986 | Buell |
| 4,597,761 A | 7/1986 | Buell |
| 4,605,403 A | 8/1986 | Tucker |
| 4,610,678 A | 9/1986 | Weisman et al. |
| 4,615,695 A | 10/1986 | Cooper |
| 4,625,001 A | 11/1986 | Tsubakimoto et al. |
| 4,654,039 A | 3/1987 | Brandt et al. |
| 4,666,983 A | 5/1987 | Tsubakimoto et al. |
| 4,695,278 A | 9/1987 | Lawson |
| 4,699,619 A | 10/1987 | Bernardin |
| 4,710,188 A | 12/1987 | Runeman |
| 4,715,918 A | 12/1987 | Lang |
| 4,734,478 A | 3/1988 | Tsubakimoto et al. |
| 4,756,709 A | 7/1988 | Stevens |
| 4,770,656 A | 9/1988 | Proxmire et al. |
| 4,773,903 A | 9/1988 | Weisman et al. |
| D298,566 S | 11/1988 | Runeman |
| 4,785,996 A | 11/1988 | Ziecker et al. |
| 4,808,178 A | 2/1989 | Aziz et al. |
| 4,816,025 A | 3/1989 | Foreman |
| 4,822,453 A | 4/1989 | Dean et al. |
| 4,826,499 A | 5/1989 | Ahr |
| 4,834,736 A | 5/1989 | Boland et al. |
| 4,834,737 A | 5/1989 | Khan |
| 4,834,738 A | 5/1989 | Kielpikowski et al. |
| 4,842,666 A | 6/1989 | Werenicz |
| 4,851,069 A | 7/1989 | Packard et al. |
| 4,872,871 A | 10/1989 | Proxmire et al. |
| 4,888,093 A | 12/1989 | Dean et al. |
| 4,892,598 A | 1/1990 | Stevens et al. |
| 4,898,642 A | 2/1990 | Moore et al. |
| 4,923,454 A | 5/1990 | Seymour et al. |
| 4,928,323 A | 5/1990 | Nathan |
| 4,938,756 A | 7/1990 | Salek |
| 4,950,264 A | 8/1990 | Osborn, III |
| 4,961,736 A | 10/1990 | McCloud |
| 4,964,857 A | 10/1990 | Osborn |
| 4,964,860 A | 10/1990 | Gipson et al. |
| 4,968,312 A | 11/1990 | Khan |
| 4,988,344 A | 1/1991 | Reising et al. |
| 4,988,345 A | 1/1991 | Reising |
| 4,994,037 A | 2/1991 | Bernardin |
| 5,009,650 A | 4/1991 | Bernardin |
| 5,009,653 A | 4/1991 | Osborn, III |
| 5,019,068 A | 5/1991 | Perez et al. |
| 5,061,259 A | 10/1991 | Goldman et al. |
| 5,069,672 A | 12/1991 | Wippler et al. |
| 5,098,423 A | 3/1992 | Pieniak et al. |
| 5,102,597 A | 4/1992 | Roe et al. |
| 5,128,082 A | 7/1992 | Makoui |
| 5,137,537 A | 8/1992 | Herron et al. |
| 5,141,505 A | 8/1992 | Barrett |
| 5,147,345 A | 9/1992 | Young et al. |
| 5,149,335 A | 9/1992 | Kellenberger et al. |
| 5,167,655 A | 12/1992 | McCoy |
| 5,176,668 A | 1/1993 | Bernardin |
| 5,181,915 A | 1/1993 | Smith |
| 5,188,624 A | 2/1993 | Young, Sr. et al. |
| 5,207,662 A | 5/1993 | James |
| 5,207,663 A | 5/1993 | McQueen |
| 5,217,445 A | 6/1993 | Young et al. |
| 5,236,428 A | 8/1993 | Zajaczkowski |
| 5,260,345 A | 11/1993 | DesMarais et al. |
| 5,268,224 A | 12/1993 | DesMarais et al. |
| 5,318,554 A | 6/1994 | Young et al. |
| 5,324,561 A | 6/1994 | Rezai et al. |
| 5,325,543 A | 7/1994 | Allen |
| 5,358,500 A | 10/1994 | Lavon et al. |
| 5,360,419 A | 11/1994 | Chen et al. |
| 5,360,422 A | 11/1994 | Brownlee et al. |
| 5,383,867 A | 1/1995 | Klinger |
| 5,387,207 A | 2/1995 | Dyer et al. |
| 5,401,266 A | 3/1995 | Runeman et al. |
| 5,405,342 A | 4/1995 | Roessler et al. |
| 5,409,476 A | 4/1995 | Coates |
| 5,458,591 A | 10/1995 | Roessler et al. |
| 5,476,457 A | 12/1995 | Roessler et al. |
| 5,486,168 A | 1/1996 | Runeman et al. |
| 5,531,728 A | 7/1996 | Lash |
| 5,549,589 A | 8/1996 | Horney et al. |
| 5,550,167 A | 8/1996 | DesMarais |
| 5,556,393 A | 9/1996 | Rönnberg |
| 5,562,646 A | 10/1996 | Goldman et al. |
| 5,563,179 A | 10/1996 | Stone et al. |
| 5,569,229 A | 10/1996 | Rogers |
| 5,599,335 A | 2/1997 | Goldman et al. |
| 5,613,959 A | 3/1997 | Roessler et al. |
| 5,636,387 A | 6/1997 | Lundy |
| 5,650,222 A | 7/1997 | DesMarais et al. |
| 5,667,503 A | 9/1997 | Roe et al. |
| 5,778,110 A | 7/1998 | Furuya |
| 5,800,416 A | 9/1998 | Seger et al. |
| 5,817,081 A | 10/1998 | LaVon et al. |
| 5,827,253 A | 10/1998 | Young et al. |
| 5,843,055 A | 12/1998 | Seger |
| 5,843,065 A | 12/1998 | Wyant |
| 5,906,602 A | 5/1999 | Weber et al. |
| 5,941,863 A | 8/1999 | Guidotti et al. |
| 6,015,935 A | 1/2000 | LaVon et al. |
| 6,083,210 A | 7/2000 | Young et al. |
| 6,229,061 B1 | 5/2001 | Dragoo et al. |
| 6,336,923 B1 | 1/2002 | Fujioka et al. |
| 6,443,933 B1 | 9/2002 | Suzuki et al. |
| 6,582,412 B2 * | 6/2003 | Christoffel et al. ...... 604/385.01 |
| 6,623,466 B1 | 9/2003 | Richardson |
| 6,689,114 B2 | 2/2004 | Bouchard et al. |
| 6,766,817 B2 | 7/2004 | da Silva |
| 6,793,649 B1 | 9/2004 | Fujioka et al. |
| 6,918,404 B2 | 7/2005 | da Silva |
| 6,989,005 B1 | 1/2006 | LaVon et al. |
| 6,989,006 B2 | 1/2006 | Lavon et al. |
| 6,996,851 B2 * | 2/2006 | Nordness et al. ............ 2/78.3 |

| | | | | | | |
|---|---|---|---|---|---|---|
| 7,066,586 | B2 | 6/2006 | da Silva | JP | 1993-86314 | 11/1993 |
| 7,285,255 | B2 | 10/2007 | Kadlec et al. | JP | 06-121812 | 5/1994 |
| 2002/0013566 | A1 | 1/2002 | Chappell et al. | WO | WO 89/11843 | 12/1989 |
| 2002/0058921 | A1 | 5/2002 | Sigl | WO | WO 91/10413 | 7/1991 |
| 2002/0091368 | A1 | 7/2002 | LaVon et al. | WO | WO 91/16871 | 11/1991 |
| 2002/0112982 | A1 | 8/2002 | Stagray et al. | WO | WO 94/24973 | 11/1994 |
| 2002/0143311 | A1 | 10/2002 | Brisebois | WO | WO 95/17870 | 7/1995 |
| 2002/0143316 | A1 | 10/2002 | Sherrod et al. | WO | WO 96/03950 A1 | 2/1996 |
| 2003/0199844 | A1 | 10/2003 | Lavon et al. | WO | WO 01/60300 A1 | 8/2001 |
| 2003/0220623 | A1 | 11/2003 | Sugiyama et al. | WO | WO 01/91685 A1 | 12/2001 |
| 2004/0024379 | A1 | 2/2004 | LaVon et al. | WO | WO 02/34184 A1 | 5/2002 |
| 2004/0030314 | A1 | 2/2004 | LaVon et al. | WO | WO 02/34185 A1 | 5/2002 |
| 2004/0039361 | A1 | 2/2004 | LaVon et al. | WO | WO 02/49838 A2 | 6/2002 |
| 2005/0256478 | A1 | 11/2005 | Genke | WO | WO 2004/049992 A2 | 6/2004 |
| 2006/0173429 | A1* | 8/2006 | Acors .......................... 604/361 | | | |
| 2007/0049895 | A1* | 3/2007 | Van Gompel et al. . 604/385.101 | | | |

FOREIGN PATENT DOCUMENTS

| | | |
|---|---|---|
| EP | 0 319 314 A2 | 6/1989 |
| EP | 0 945 110 A2 | 9/1999 |
| GB | 493819 | 10/1938 |
| GB | 734994 | 8/1955 |
| GB | 1 411 087 | 10/1975 |
| GB | 2 042 342 | 9/1980 |
| GB | 2 269 998 | 3/1994 |
| GB | 2 295 321 A | 5/1996 |

OTHER PUBLICATIONS

U.S. Appl. No. 11/598,308, filed Nov. 13, 2006, Burns, Jr., et al.
U.S. Appl. No. 11/598,462, filed Nov. 13, 2006, Beck, et al.
U.S. Appl. No. 11/598,406, filed Nov. 13, 2006, Beck, et al.
International Search Report for PCT/IB2007/054369 of Apr. 1, 2008.
U.S. Appl. No. 11/588,135, filed Oct. 26, 2006, Office Action, Apr. 1, 2009, 5 pages.
U.S. Appl. No. 11/588,135, filed Oct. 26, 2006, Amendment, Jun. 7, 2010, 8 pages.

* cited by examiner

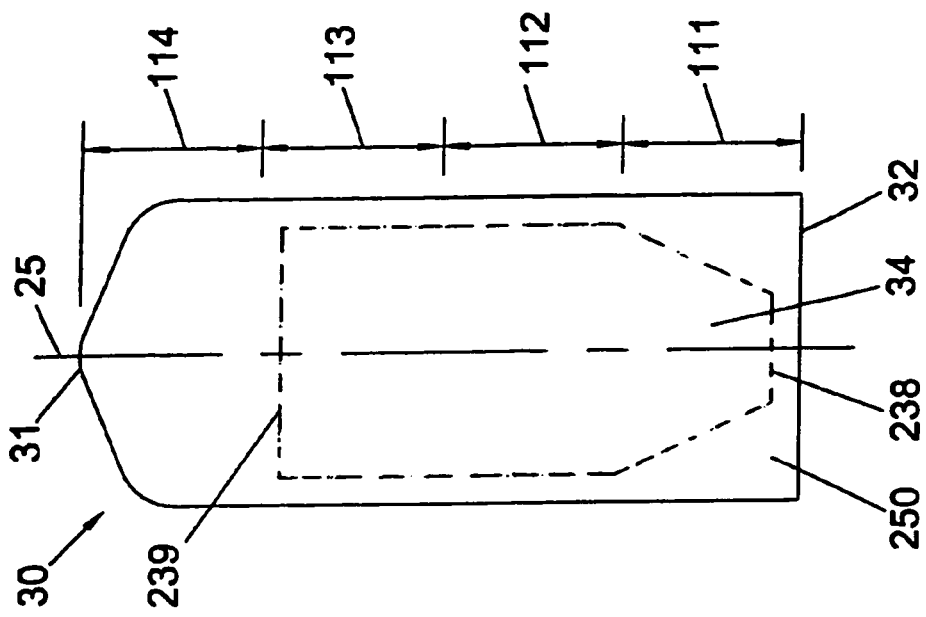
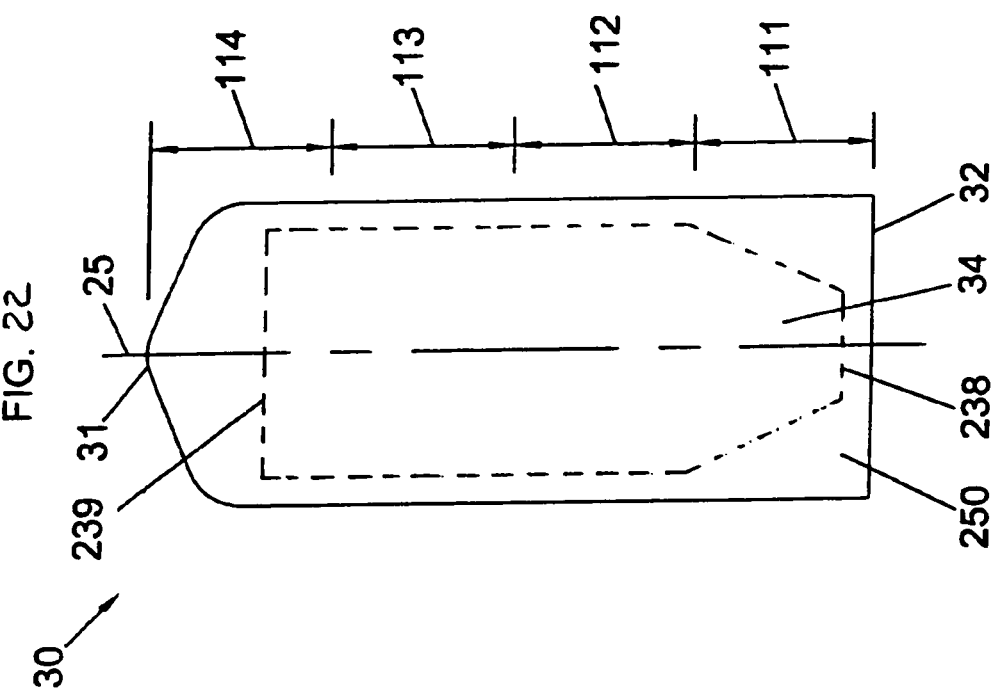

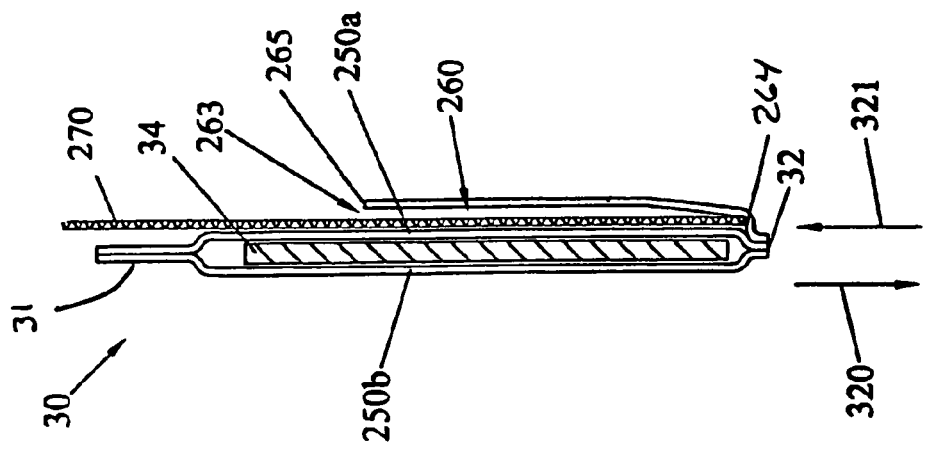
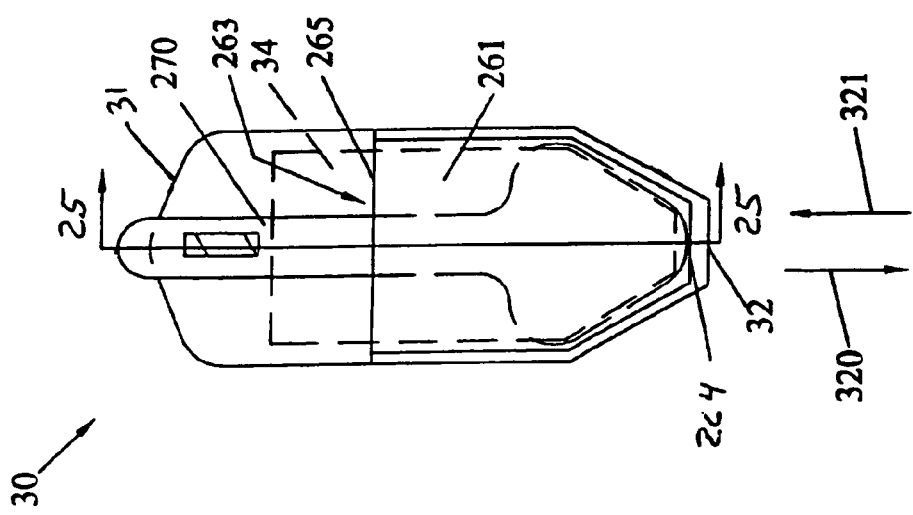

METHOD FOR USING A DISPOSABLE ABSORBENT ARTICLE AS A SWIM PANT

FIELD OF THE INVENTION

The present disclosure relates to disposable absorbent articles, and more particularly, to methods for using disposable absorbent articles having replaceable absorbent core components as a swim pant.

BACKGROUND OF THE INVENTION

Disposable absorbent articles such as disposable diapers, incontinence pads, training pants, and catamenial napkins generally include an absorbent core for receiving and holding bodily exudates. In everyday use, a disposable diaper may be worn until the absorbent core is saturated with bodily exudates. Once the core is saturated, the disposable diaper can be removed from the wearer, disposed of, and replaced with a fresh diaper. Advances in manufacturing techniques and the application of new materials have allowed the development of disposable diapers with increased absorbency and comfort for the wearer. As such, some disposable diapers are provided with absorbent cores capable of receiving and holding more bodily exudates than previously possible.

Disposable diapers configured with highly absorbent cores may provide benefits by being able to absorb relatively large amounts of bodily exudates. However, high absorbency diapers may not be well adapted for use in some situations. For example, when worn in a swimming pool, a highly absorbent core will absorb and hold large quantities of water, making the diaper uncomfortable, heavy, and/or otherwise hindering the wearer's mobility. In recent years, disposable swim diapers have increased in popularity with some people. Many such swim diapers are adapted to be worn by children while swimming at a pool, lake, or otherwise engaging in activities in the water. Because the swim diapers are generally intended to be worn in the water, swim diapers may be constructed with absorbent cores having a lower absorbency than the absorbent cores provided in disposable diapers configured for everyday use (e.g. receiving and holding bodily exudates). As such, the absorbent core on a swim diaper will absorb and hold relatively less water.

Although the swim diapers provide certain advantages by absorbing less water, there are some disadvantages associated with such diapers. For example, because some swim diapers are configured with a core having a relatively low absorbency, such swim diapers may absorb and hold relatively small amounts of bodily exudates. As such, some swim diapers may become more easily saturated with bodily exudates and may be prone to leakage when worn outside the water. Therefore, a parent or other caregiver may be required to perform several diaper changes on a child when engaging in activities involving water, such as swimming. For example, a caregiver may want a child to wear a high absorbency diaper while traveling to a pool. Once at the pool, a caregiver may remove and replace the child's high absorbency diaper with a swim diaper. After wearing the swim diaper in the water, the absorbent core may eventually become saturated or waterlogged and may no longer effectively absorb and hold bodily exudates. Therefore, upon exiting the water and before engaging in other activities outside the water, a waterlogged swim diaper may need to be replaced with a fresh, dry high absorbency diaper or a fresh, dry swim diaper. Before traveling home from the pool, the caregiver may need to again remove and replace the child's swim diaper with a fresh, dry high absorbency diaper. In these scenarios, a parent or other caregiver may be required to perform diaper changes in public, such as on a pool deck. In other scenarios, diaper changes may have to be performed in a locker room or public restroom, which may unclean. Diaper changes in such public places as well as the number of diaper changes can become inconvenient for the caregiver and child alike. In one example of a situation involving multiple children of different sexes, it may be uncomfortable or inconvenient to change diapers in locker rooms designated as "mens" and "womens."

SUMMARY OF THE INVENTION

Aspects of the present disclosure involve new methods for using disposable absorbent articles having replaceable absorbent core components as a swim pant. One or more low absorbency, potentially non-removable, absorbent core components may be disposed in a chassis of the disposable absorbent article, such as in a crotch region. The absorbent article may also include replaceable absorbent core components adapted to be selectively disposed in capillary liquid communication with the low absorbency, potentially non-removable, absorbent core component. Embodiments of such absorbent articles can be configured for use as a swim pant or diaper with relatively low absorbency by removing the replaceable absorbent core component. As discussed below, removal of the replaceable core component can be done without having to remove the absorbent article from the wearer. In addition, embodiments of the absorbent articles can be reconfigured for use as a high absorbency diaper by reinstalling a replaceable absorbent core component without having to remove the absorbent article from the wearer. Aspects of the disclosure herein provides for new uses of absorbent articles as a swim diaper with the replaceable core components removed.

In one aspect, a method for using an article of commerce as a swim pant includes the step of wearing a disposable absorbent article comprising: a chassis including an inner surface and an outer surface and forming a waist opening and a pair of leg openings, the chassis having longitudinally opposing first and second waist end edges, longitudinally opposing first and second waist regions adjacent to the respective waist end edges, and a crotch region longitudinally intermediate of the waist regions; and at least one absorbent core component disposed adjacent the inner surface. The method further includes the steps of: engaging in a water-related activity; saturating the at least one absorbent core component with water; and removing water from the at least one absorbent core component by placing a replaceable absorbent core component in liquid communication with the at least one absorbent core component.

In another aspect, a method for using an article of commerce as a swim pant includes the step of wearing a disposable absorbent article comprising: a chassis; at least one absorbent core component disposed within the chassis; wherein the disposable absorbent article is selectively configured in a high absorbency configuration by placing a second absorbent core component in liquid communication with the at least one absorbent core component; and wherein the disposable absorbent article is selectively configured in a swim configuration by removing the second absorbent core component from liquid communication with the at least one absorbent core component. The method further includes the step of engaging in a water-related activity with the disposable absorbent article in the swim configuration.

In yet another aspect, a method for using an article of commerce as a swim pant including the step of wearing a diaper configurable between a high absorbency configuration and a swim configuration, the diaper comprising: a chassis;

and a first absorbent core component disposed within the chassis; wherein the diaper is selectively configured in the high absorbency configuration by placing a second absorbent core component in liquid communication with the first absorbent core component; and wherein the diaper is selectively configured in the swim configuration by removing the second absorbent core component from liquid communication with the first absorbent core component. The method further includes the step of selectively configuring the diaper between the high absorbency configuration and the swim configuration.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

FIG. 22 is a plan view showing an absorbent layer of a replaceable absorbent core component illustratively divided into four longitudinal segments;

FIG. 23 is a plan view showing another absorbent layer of a replaceable absorbent core component illustratively divided into four longitudinal segments;

FIG. 24 is a plan view showing a replaceable absorbent core component having an insertion tool disposed in an insertion pocket;

FIG. 25 is a partial section view showing the replaceable absorbent core component of FIG. 24;

DETAILED DESCRIPTION OF THE INVENTION

Figure 1:
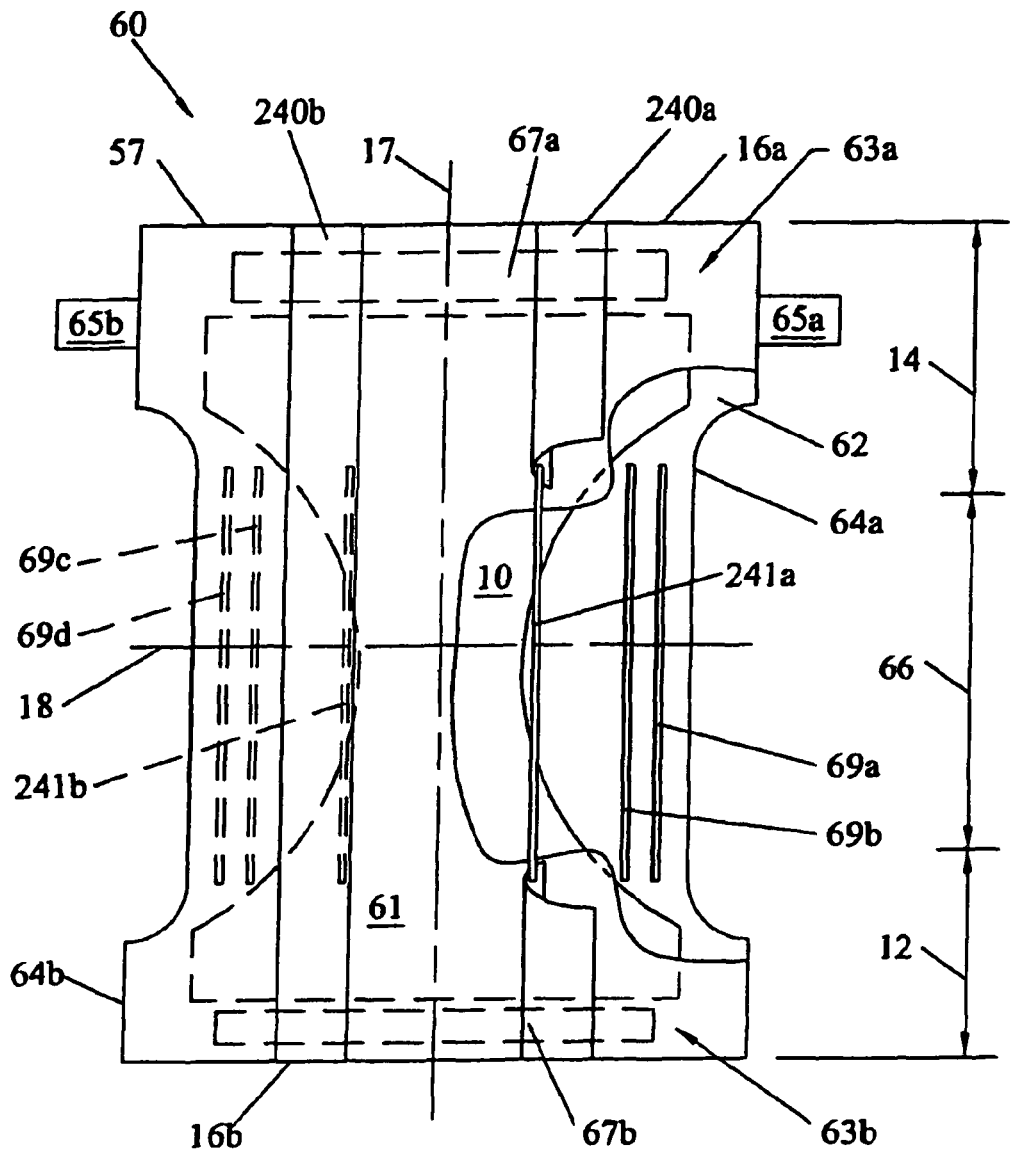
FIG. 1 is a plan view of an exemplary diaper in its flat-out, uncontracted state, i.e., with all elastic induced contraction pulled out, with portions of the structure being cut away to more clearly show the construction of the diaper, and with the portion of the diaper that contacts the wearer facing the viewer.

Aspects of the present disclosure involve new methods for using disposable absorbent articles having replaceable absorbent core components as a swim pant. Advances in disposable absorbent article design have led to the development of absorbent articles having one or more replaceable absorbent core components. In some configurations, the absorbent core component can be replaced without having to remove the absorbent article from the wearer. In one example, a disposable absorbent article may be adapted to be worn about a lower torso of a human body. The absorbent article may include a chassis forming a waist opening and a pair of leg openings. The chassis may have longitudinally opposed waist end edges, longitudinally opposed waist regions, and a crotch region longitudinally intermediate of the waist regions. One or more low absorbency absorbent core components may be disposed in the chassis, such as in the crotch region. In some embodiments, the low absorbency absorbent core components are configured as non-removable absorbent core components. The absorbent article may also include one or more replaceable absorbent core components selectively disposed in capillary liquid communication with the low absorbency absorbent core component. The removable core component may be selectively placed in capillary liquid communication with the low absorbency absorbent core component prior to the application of the absorbent article to the wearer or while the absorbent article is being worn. As discussed in more detail below, embodiments of such absorbent articles can be configured for use as a swim pant or diaper with relatively low absorbency by removing the replaceable absorbent core component. Removal of the replaceable core component can be done without having to remove the absorbent article from the wearer. In addition, embodiments of the absorbent articles can be reconfigured for use as a high absorbency diaper by reinstalling a replaceable absorbent core component without having to remove the absorbent article from the wearer.

Although various embodiments of absorbent articles having replaceable core components have been disclosed in the past, the normal and usual uses of such absorbent articles have been focused primarily on using the absorbent articles with the replaceable core component installed. For example, absorbent articles are worn with the replaceable core components installed to receive and hold bodily exudates. When the core components become saturated with bodily discharges, such as urine, the replaceable core components can be removed and replaced with a fresh replaceable core component for continued use of the absorbent article. As such, previously disclosed uses of absorbent articles having replaceable core components chiefly involved wearing the absorbent article with the replaceable core component installed, as opposed to wearing the absorbent article with the replaceable core component removed. Aspects of the disclosure herein provides for new uses of absorbent articles with the replaceable core components removed. In one aspect, the present disclosure provides for using and wearing absorbent articles as a swim pant with the replaceable core component removed. As discussed below, the new application and/or use of an absorbent article with replaceable core components as a swim pant provide various benefits, not previously realized. Such benefits may include, for example, the ability to convert a high absorbency diaper into a swim diaper and back again without having to remove the diaper from a wearer. Other benefits may relate to using a replaceable core component to extract water from a waterlogged low absorbency, non-removable, core component without having to remove the diaper from a wearer.

The following provides a detailed description of structural aspects of various embodiments of disposable absorbent articles for use in the presently disclosed methods. It is to be appreciated that other configurations of disposable absorbent articles with replaceable core components can also be used.

The disclosures of all patents, patent applications, and any patents which issue thereon, as well as any corresponding published foreign patent applications, and all publications listed and/or referenced hereafter in this description, are hereby incorporated herein by reference. It is expressly not admitted, however, that any of the documents or any combination of the documents incorporated herein by reference teaches or discloses the present invention.

LIST OF U.S. PATENT REFERENCES

U.S. Pat. No. 3,848,594 to Buell, issued 19 Nov. 1974
U.S. Pat. No. 3,860,003 to Buell, issued 14 Jan. 1975
U.S. Pat. No. 4,062,817 to Westerman, issued 13 Dec. 1977
U.S. Pat. No. 4,076,663 to Masuda et al., issued 28 Feb. 1978
U.S. Pat. No. 4,081,301 to Buell, issued 28 Mar. 1978
U.S. Pat. No. 4,260,443 to Lindsay et al., issued 7 Apr. 1981
U.S. Pat. No. 4,467,012 to Pedersen et al., issued 21 Aug. 1984
U.S. Pat. No. 4,515,595 to Kievit et al., issued 7 May 1985
U.S. Pat. No. 4,625,001 to Tsubakimoto et al., issued 25 Nov. 1986
U.S. Pat. No. 4,666,983 to Tsubakimoto et al., issued 19 May 1987
U.S. Pat. No. 4,681,580 to Reising et al., issued 21 Jul. 1987
U.S. Pat. No. 4,695,278 to Lawson, issued 22 Sep. 1987
U.S. Pat. No. 4,715,918 to Lang, issued 29 Dec. 1987
U.S. Pat. No. 4,773,903 to Weisman et al., issued 27 Sep. 1988
U.S. Pat. No. 4,795,454 to Dragoo, issued 3 Jan. 1989
U.S. Pat. No. 4,808,178 to Aziz et al., issued 28 Feb. 1989
U.S. Pat. No. 4,816,025 to Foreman, issued 28 Mar. 1989
U.S. Pat. No. 4,822,453 to Dean et al., issued 18 Apr. 1989
U.S. Pat. No. 4,851,069 to Packard et al., issued 25 Jul. 1989
U.S. Pat. No. 4,888,093 to Dean et al., issued 19 Dec. 1989
U.S. Pat. No. 4,892,536 to DesMarais et al., issued 9 Jan. 1990
U.S. Pat. No. 4,898,642 to Moore et al., issued 6 Feb. 1990
U.S. Pat. No. 4,923,454, to Seymour et al., issued 8 May 1990
U.S. Pat. No. 4,950,264 to Osborn, issued 21 Aug. 1990
U.S. Pat. No. 4,988,344 to Reising et al., issued 29 Jan. 1991
U.S. Pat. No. 4,988,345 to Reising, issued 29 Jan. 1991
U.S. Pat. No. 4,990,147 to Freeland, issued 5 Feb. 1991
U.S. Pat. No. 4,994,037 to Bemardin, issued 19 Feb. 1991
U.S. Pat. No. 5,009,650 to Bemardin, issued 23 Apr. 1991
U.S. Pat. No. 5,009,653 to Osborn, issued 23 Apr. 1991
U.S. Pat. No. 5,037,416 to Allen et al., issued 6 Aug. 1991
U.S. Pat. No. 5,061,259 to Goldman et. al, issued 29 Oct. 1991
U.S. Pat. No. 5,102,597 to Roe et al., issued 7 Apr. 1992
U.S. Pat. No. 5,128,082 to Makoui, issued 7 Jul. 1992
U.S. Pat. No. 5,137,537 to Herron et al., issued 11 Aug. 1992
U.S. Pat. No. 5,143,679 to Weber et al., issued 1 Sep. 1992
U.S. Pat. No. 5,147,345 to Young et al., issued 15 Sep. 1992
U.S. Pat. No. 5,149,335 to Kellenberger et al., issued Sep. 22, 1992
U.S. Pat. No. 5,151,092 to Buell et al., issued 29 Sep. 1992
U.S. Pat. No. 5,156,793 to Buell et al., issued 20 Oct. 1992
U.S. Pat. No. 5,167,897 to Weber et al., issued 1 Dec. 1992
U.S. Pat. No. 5,176,668 to Bemardin, issued 5 Jan. 1993
U.S. Pat. No. 5,217,445 to Young et al., issued 8 Jun. 1993
U.S. Pat. No. 5,221,274 to Buell et al., issued 22 Jun. 1993
U.S. Pat. No. 5,260,345 to DesMarais et al., issued 9 Nov. 1993
U.S. Pat. No. 5,268,224 to DesMarais et al., issued 7 Dec. 1993
U.S. Pat. No. 5,269,775 to Freeland et al., issued 14 Dec. 1993
U.S. Pat. No. 5,324,561 to Rezai et al., issued 28 Jun. 1994
U.S. Pat. No. 5,358,500 to LaVon et al., issued 25 Oct. 1994
U.S. Pat. No. 5,387,207 to Dyer et al., issued 7 Feb. 1995
U.S. Pat. No. 5,531,728 to Lash, isseued 2 Jul. 1996
U.S. Pat. No. 5,549,589 to Homey et al., issued 27 Aug. 1996
U.S. Pat. No. 5,550,167 to Des Marais et al., issued 27 Aug. 1996
U.S. Pat. No. 5,554,145 to Roe et al., issued 10 Sep. 1996
U.S. Pat. No. 5,562,646 to Goldman et al., issued 8 Oct. 1996
U.S. Pat. No. 5,563,179 to Stone et al., issued 18 Oct. 1996
U.S. Pat. No. 5,569,234 to Buell et al., issued 29 Oct. 1996
U.S. Pat. No. 5,571,096 to Dobrin et al., issued 5 Nov. 1996
U.S. Pat. No. 5,817,081 to LaVon et al., issued 6 Oct. 1998
U.S. Pat. No. 5,599,335 to Goldman et al., issued 4 Feb. 1997
U.S. Pat. No. 5,650,222 to DesMarais et al., issued 22 Jul. 1997
U.S. Pat. No. 5,800,416 to Seger et al., issued 1 Sep. 1998
U.S. Pat. No. 5,843,055 to Seger et al., issued 1 Dec. 1998
U.S. Pat. No. 5,865,823 to Curro, issued 2 Feb. 1999
U.S. Pat. No. 5,897,545 to Kline et al., issued 27 Apr. 1999
U.S. Pat. No. 5,906,602 to Weber et al., issued 25 May 1999
U.S. Pat. No. 6,004,306 to Robles et al., issued 21 Dec. 1999
U.S. Pat. No. 6,120,487 to Ashton, issued 19 Oct. 2000
U.S. Pat. No. 6,187,696 to Lim et al., issued 13 Feb. 2001
U.S. Pat. No. 6,251,097 to Kline et al., issued 26 Jun. 2001
U.S. Pat. No. 6,432,098 to Kline et al., issued 13 Aug. 2002

U.S. Patent Application Publication US2003/0199844A1, published 23 Oct. 2003

Definitions

The following definitions of terms may be useful for understanding the following disclosure.

Absorbent article: A device that absorbs and contains bodily exudates by means of an absorbent core, and, more specifically, a device which is placed against or in proximity to the body of a wearer to absorb and contain the various exudates discharged from the body. An exemplary embodiment of an absorbent article is the disposable absorbent article, diaper 60, as shown in the drawing figures. It should be understood, however, that the present disclosure is also applicable to other absorbent articles such as incontinence briefs, incontinence undergarments, diaper holders and liners, training pants, pull-on diapers, swim diapers, and the like.

Absorbent core: An element of an absorbent article containing a material or a combination of materials suitable for absorbing, distributing, and storing aqueous liquids such as bodily exudates.

Absorbent core component: A structural constituent of an absorbent core, e.g., a piece of an absorbent core, such as one of multiple pieces in a multi-piece absorbent core.

Absorbent layer: A term referring to a discrete, identifiable sheet-like or web-like element of an absorbent core structure which may remain detached and relatively movable with respect to another such element or may be bonded or joined so as to remain permanently associated with another such element. Each absorbent layer may itself include a laminate or combination of several sheets or webs of similar or diverse compositions. Absorbent member: A functional constituent of an absorbent core, e.g., a liquid acquisition member, a liquid acquisition/distribution member, or a liquid storage/redistribution member formed of a material or materials having particular liquid handling characteristics suitable for the specific function.

Absorbent insert: A device adapted for insertion into an absorbent article and to serve as an absorbent core component when so inserted. A replaceable absorbent core component is an absorbent insert, the latter term being especially descriptive when referring to the device alone.

Chassis: A foundational constituent of an absorbent article upon which the remainder of the structure of the article is built up or overlaid, e.g., in a diaper, the structural elements that give the diaper the form of briefs or short pants when configured for wearing, such as a backsheet, a top sheet, or a combination of a top sheet and a backsheet.

Diaper: An absorbent article generally worn by infants and incontinent persons about the lower torso of the wearer.

Disposable: A term used to describe absorbent articles that are not intended to be laundered or otherwise restored or reused as an absorbent article after use, i.e., that are intended to be discarded after a single use and may be recycled, composted or otherwise disposed of in an environmentally compatible manner. Note that, as described in this disclosure, a single use of a chassis and a non-removable core component may correspond to several uses and replacements of replaceable core components.

Capillary liquid communication: The flow of a liquid from one absorbent element to another absorbent element by capillary transport. Also, a term used to describe a structural disposition of absorbent elements in which the flow of a liquid from one of the absorbent elements to the other occurs through capillary transport of the liquid, generally requiring either the direct face-to-face contact of the absorbent elements with each other, the direct face-to-face contact of each of the absorbent elements with a hydrophilic intermediate layer providing capillary conduction of the liquid from one absorbent element to the other, or the protrusion of the fibers of a fibrous absorbent element through a porous and/or permeable intermediate layer into contact with the other absorbent element.

Join, joined, joining: Terms encompassing configurations wherein an element is directly secured to another element by affixing the element directly to the other element, as well as configurations wherein the element is indirectly secured to the other element by affixing the element to an intermediate member or members which in turn is or are affixed to the other element.

Major surface: A term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

Replaceable: A term used to describe a component of an absorbent article that can be replaced, that is, a component that can be removed and for which a like component or a component providing similar functionality can be substituted in place of the removed component, e.g., a replaceable absorbent core component or absorbent insert.

Stratum, stratified: Terms referring herein to overlying or superimposed regions within a given layer or structure which have identifiably diverse compositions, densities, or other material properties such that the layer or structure is non-homogeneous through a cross section from one surface to an opposing surface.

Wearer-facing layer: The elements of the chassis that form the inner surface of the absorbent article, such as the topsheet, the leg cuffs, and the side panels, etc., when such elements are present.

Garment-facing layer: The elements of the chassis that form the outer surface of the absorbent article, such as the backsheet, the side panels, the waist fasteners, and the like, when such elements are present.

Overview of Absorbent Articles

As described below in detail, the present disclosure relates to absorbent articles suitable for absorbing and retaining aqueous bodily liquids. These absorbent articles may include a backsheet formed of a substantially liquid impervious material and an absorbent core disposed adjacent to the backsheet. The absorbent core may include at least one removable core component disposed in capillary liquid communication with at least one low absorbency core component. The low absorbency core component may also be non-removable. The removable core component may be inserted into the absorbent article prior to the application of the absorbent article to the wearer or while the absorbent article is being worn. When the removable core component or a member thereof is removed, a replacement absorbent core component or member may be inserted in place of the removed component or member.

In some exemplary embodiments, the absorbent article may include a plurality of absorbent core components, including a front panel and a rear panel in capillary liquid communication with a center section. Each of the absorbent core components may include multiple absorbent layers. Upon saturation with bodily discharges and/or water, removable components or absorbent layers of the absorbent core may be removed from the absorbent article. New, unsaturated absorbent core components or absorbent layers may then be positioned in place of the removed saturated core components or absorbent layers.

In some exemplary embodiments, the removable core component is disposed adjacent to the body-facing surface of the backsheet and is accessible through an aperture in the backsheet. In other exemplary embodiments, the removable core component is disposed adjacent to the garment-facing surface of the backsheet and is contained in a pocket formed by a piece of sheet material affixed to the outer surface of the backsheet.

In some exemplary embodiments, the absorbent article includes a liquid pervious topsheet and a substantially liquid impervious backsheet joined to the topsheet about the periphery of the absorbent article. In a predetermined area of the periphery, the topsheet and the backsheet may be separated to form an opening providing access to a removable core component disposed between the topsheet and the backsheet and for the insertion of a replacement core component.

In some exemplary embodiments, the center absorbent core component may have suitable liquid acquisition and/or acquisition/distribution characteristics, while the front and rear absorbent core panels or components may have suitable storage/redistribution characteristics.

Exemplary Diaper Embodiment

Figure 2:
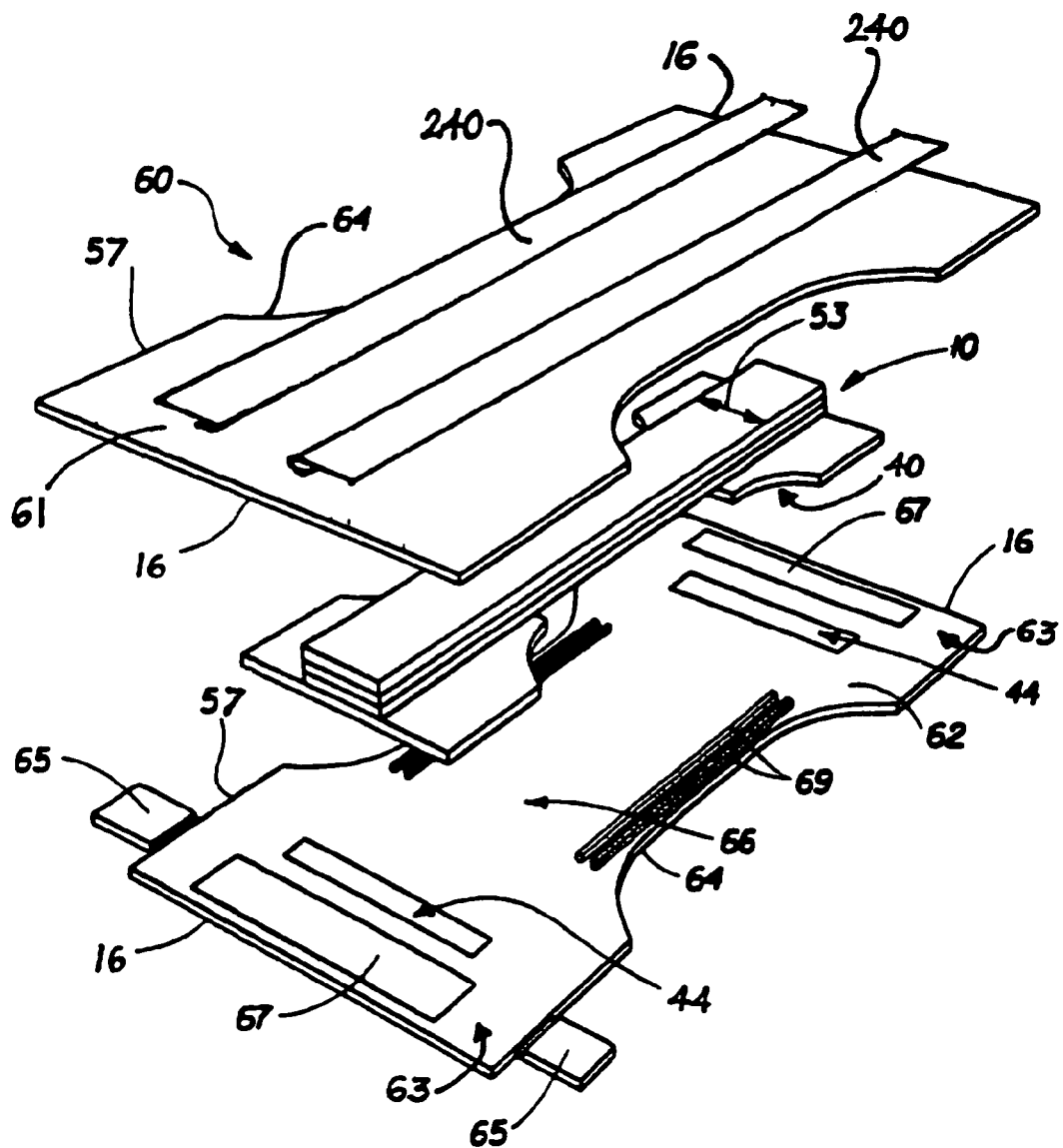
FIG. 2 is an exploded perspective view depicting an exemplary absorbent article, with the portion of the article that contacts the wearer facing upward.

FIG. 1 is a plan view of an exemplary embodiment of an absorbent article and shows exemplary diaper 60 in its flat-out, uncontracted state, i.e., with all elastic induced contraction pulled out, with portions of the structure being cut away to more clearly show the construction of the diaper, and with the portion of the diaper which contacts the wearer facing the viewer. FIG. 2 also shows an exemplary diaper 60 in an exploded perspective view, with the portion that contacts the wearer on top. In these exemplary embodiments, the diaper is shown to have a periphery 57 defined by the outer edges of the diaper, with the longitudinal edges being designated 64 and the waist end edges being designated 16. The diaper additionally has a lateral centerline which is designated 18 and a longitudinal centerline which is designated 17. The front waist region 12 and the back waist region 14 extend, respectively, from the waist end edges 16 toward the lateral centerline 18 a distance from about ¼ to about ⅓ the length of the diaper. The waist regions form those portions of the diaper which, when worn, encircle the waist of the wearer. The crotch region 66 is that portion of the diaper between the waist regions, and forms that portion of the diaper which, when worn, is positioned between the legs of the wearer and covers the lower torso of the wearer.

Figure 3:
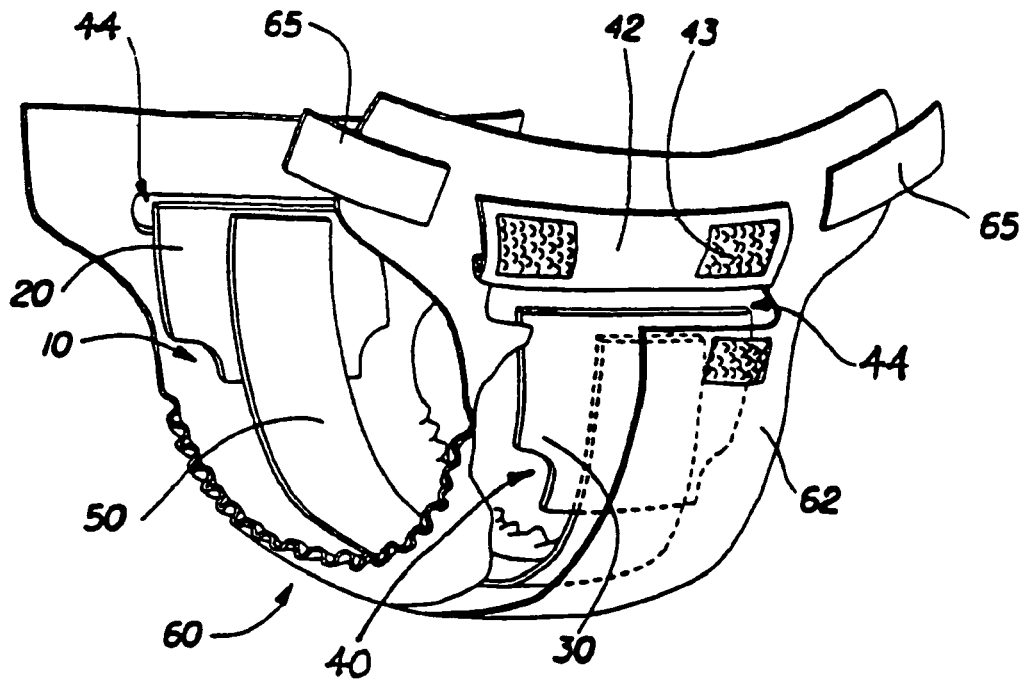
FIG. 3 is a perspective, partially segmented illustration of an exemplary diaper embodiment of an absorbent article.
Figure 4:
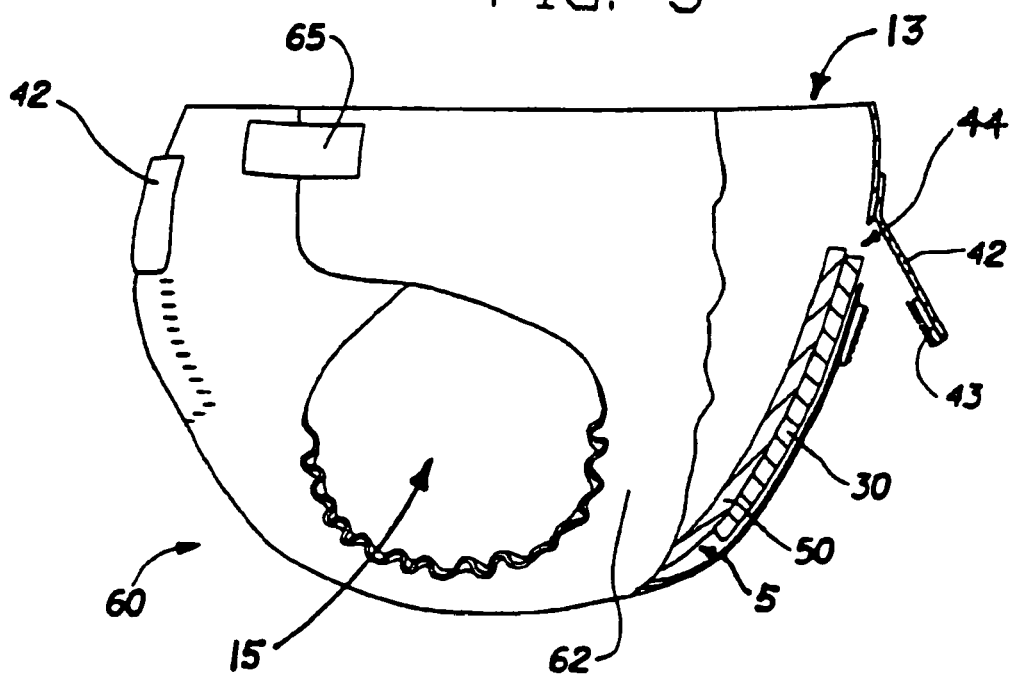
FIG. 4 is a side view, showing in partial cross-section, the exemplary absorbent article of FIG. 3.

Another exemplary disposable diaper 60 embodiment of an absorbent article is shown in partially segmented perspective view in FIG. 3 and in a side view, partial cross-section in FIG. 4. The multi-piece absorbent core 10 including multiple absorbent core components, such as the center section 50, the front panel 20, and the back panel 30, is more fully illustrated and described below. The multi-piece absorbent core is also described in the Weber et al. '602 patent.

Absorbent articles having a multi-piece absorbent core having discrete components may provide various benefits. First, the core may exhibit desirable aesthetics and fit when used in an absorbent article due to the use of discontinuous absorbent layers or panels of absorbent material. For example, the center section may include separate absorbent layers, allowing the center section to bend and buckle somewhat independently from adjacent absorbent layers and the front and rear panels and thereby provide better fit and comfort in the crotch area than is typically achieved with one-piece absorbent cores.

Another advantage provided by a multi-piece absorbent core is the ability to independently vary selected characteristics of the absorbent core components and members. The characteristics that may be varied include the acquisition rates, distribution rates, storage capacities and rates, interfacial liquid transfer rates and efficiencies, thickness, functionality, and the shape or configuration of the absorbent layers or panels. For example, in an exemplary embodiment of an absorbent article, three absorbent layers may form the center section, with the absorbent layer closest to the body of the wearer having relatively greater acquisition characteristics than the remaining two outer absorbent layers having relatively greater acquisition/distribution characteristics. In this configuration, bodily discharges such as urine are quickly acquired by the body-side absorbent layer serving as an acquisition member and then desorbed into the adjacent absorbent layers serving as acquisition/distribution members for distribution to the front and back panels, which may have greater storage/redistribution characteristics.

Yet another benefit resulting from the use of a multi-piece absorbent core in an absorbent article is the capability of removing and/or replacing components of the absorbent core to regenerate the storage/redistribution capacity of the absorbent core. The provision of access to the removable absorbent core components, for example, to the back panel, allows the removal and/or replacement of those absorbent core components. In this disclosure, all description of the back panels, their removal and replacement, and access to them for their removal and replacement, is generally applicable to the front panels and vice versa, in various exemplary embodiments.

By replacing absorbent core components, particularly absorbent core components that are primarily suited for storage/redistribution, the use of the absorbent article, such as the disposable diaper, may be prolonged while continuing to draw moisture away from the wearer's skin. As storage/redistribution absorbent core members in, e.g., the front panel and the back panel, become saturated, they may become substantially less effective at absorbing moisture from acquisition/distribution members in the center section. Consequently, the center section becomes more saturated, thereby hindering its ability to absorb as much moisture away from the wearer's skin. However, once an absorbent core component such as the back panel is replaced, the absorbent suction of that absorbent core component is regenerated, and it once again becomes capable of absorbing moisture from the acquisition/distribution member of the center section. Therefore, the disposable diaper may be worn longer, and regeneration of the absorbent core may be made without removal of the diaper from the wearer. It should be understood that the absorbent core described herein may also be useful for other absorbent articles such as incontinent briefs, incontinent pads, training pants, and the like.

As described throughout this disclosure, specific components of the multi-piece absorbent core are removable and replaceable in absorbent articles. For instance, the front panel 20 and/or the back panel 30 may be removable and replaceable, while another component, such as the center section 50, may be non-removably disposed in any of the previously known configurations and thereby be made non-removable from the absorbent article. Thus, absorbent articles may have both non-removable absorbent core components and absorbent core components that are removable and replaceable.

As described in the incorporated references, components of the absorbent core may be made non-removable from the chassis by being secured, attached, affixed, and/or sandwiched to or in the chassis. For example, as described in the Buell '003 patent, an absorbent core component can be rendered immobile by, for example, bonding the backsheet and the absorbent core component together, bonding the absorbent core component to a topsheet and the topsheet to the backsheet, or tightly sandwiching the absorbent core component between a topsheet and the backsheet. Also, as described in the Lawson '278 patent, an absorbent core component may be superimposed on the backsheet and attached thereto by attachment means such as those well known in the art. For example, the absorbent core component may be secured to the backsheet by a uniform continuous layer of adhesive, a patterned layer of adhesive, or an array of separate lines or spots of adhesive. In some exemplary embodiments, an absorbent core component may be affixed in the crotch area of the chassis, as described in the DesMarais et al. '345 patent. Similarly, as described in the Osborn '264 patent, an absorbent core component may be attached over the core's upper or lower major surfaces, respectively, to adjacent members such as the topsheet and the backsheet by any of the means well known in the art, such as by spray-gluing or lines or spots of adhesive. In fact, such attachment may facilitate the integrity and recoverability of the absorbent materials while in use so as to maintain an optimum degree of absorbency.

In some exemplary embodiments, a non-removable absorbent core component, such as the center section, may be joined to the chassis in a portion of the crotch region by affixing the non-removable core component to the topsheet or the backsheet or to both the topsheet and the backsheet. For example, the non-removable core component may be joined at the crotch point to the chassis. The end portions of the non-removable core component, i.e., the portions extending from the crotch region toward the front and back waist regions, may remain unattached to the chassis and thereby be free to "float" within the absorbent article. Alternatively, the front portion of the non-removable core component may be affixed to the chassis and only the rear portion may be allowed to float. This floating core configuration allows the unattached portion of the non-removable core component to slide relative to the backsheet and or the topsheet when the absorbent article is applied to the wearer. The floating core configuration also allows the unattached portion of the non-removable core component to slide in response to the contraction of the chassis caused by the elastics in the leg cuff regions of the absorbent article. Allowing a portion of the non-removable core component to slide relative to the chassis may avoid the folding and wrinkling of the non-removable core component that typically occurs in absorbent articles having the entire non-removable core component affixed to the distorted and/or contracted chassis.

The Absorbent Article Chassis

As described throughout this disclosure, the liquid absorbent core can be utilized in disposable absorbent products which are capable of absorbing significant quantities of bodily liquids, such as urine, perspiration, menses, and water in bodily wastes. These disposable absorbent articles may be prepared in the form of disposable diapers, adult incontinence briefs, training pants, and the like. Such form-fitting articles will generally include a flexible substrate fashioned into a chassis in the form of briefs or shorts when configured for wearing. A flexible substrate which forms the chassis of such a form-fitting article may include cloth or paper or other kinds of nonwoven substrate or formed films and may be elasticized or otherwise extensible. The chassis may be the foundational element upon which the remainder of the structure of the article is built up or overlaid.

Because the designs of the chassis and the absorbent core may be interrelated, the absorbent core is included in the following description in order to make the structural relationship between the two clear. A more detailed description of the absorbent core, itself, may be found in the next section of this disclosure.

In the exemplary embodiments shown in FIG. 1 and FIG. 2, the diaper has a substantially liquid impervious backsheet 62. On top of this backsheet is disposed an absorbent core 10 which may include one or more discrete absorbent layers and may include a superabsorbent material in one or more of the absorbent layers. On top of this absorbent core and joined to the backsheet is a fluid pervious topsheet 61. The topsheet is the element of the article that is placed next to the skin of the wearer. Additional structural features such as elastic members and fastening means for securing the diaper in place upon a wearer, such as tape tab fasteners, may also be included, as will be described below.

In these exemplary embodiments, the topsheet and the backsheet are coextensive and have length and width dimensions generally larger than those of the absorbent core. The topsheet is joined with and superimposed on the backsheet, thereby forming the chassis. While the topsheet, the backsheet, and the absorbent core can be assembled in a variety of well known configurations, an exemplary diaper configuration is described generally in the Buell '003 patent. Alternative exemplary configurations for disposable diapers herein are also disclosed in the Aziz et al. '178 patent; the Lawson '278 patent; and the Foreman '025 patent.

The backsheet may be made of a material substantially impervious to liquids and may be manufactured from a thin plastic film, although other flexible liquid impervious materials may also be used. The backsheet may be adapted to prevent the exudates absorbed and contained in the absorbent core from wetting articles, such as bed sheets and undergarments, which contact the diaper. An exemplary backsheet may be made of polyethylene film having a thickness from about 0.013 mm (0.5 mil) to about 0.051 mm (2.0 mils), although other flexible liquid impervious materials can be used. As used herein, the term "flexible" refers to materials which are compliant and which will readily conform to the general shape and contour of the wearer's body. In some embodiments, the backsheet includes two materials, a liquid impervious barrier film and a textile-like nonwoven. The barrier film may include a blend of polyolefin plastic and calcium carbonate which has been stretched to open micropores so that water vapor can pass, but liquid water cannot. Such a material is available from Clopay, 8585 Duke Boulevard, Mason, Ohio 45040, as 18 gsm BR-124. The nonwoven may be a thermally point bonded spunbound made of polypropylene. Such a material may have a basis weight of 18 gsm and is available from Fiberweb Nonwovens, 844 Southeast Main Street, Simpsonville, S.C. 29681, as 053MXXP0090 White Hydrophobic or from Avgol Nonwovens Ltd. (USA), 178 Avgol Drive, Mocksville, N.C. 27028, as 70-015-126. These two materials may be adhesively laminated together using about 1.5 grams/square meter of a hot melt adhesive.

At least a portion of the backsheet may be subjected to mechanical stretching to make it elongatable or drawable in order to provide a "zero strain" stretch laminate for, for example, forming elastic side panels. Suitable equipment and processes for such mechanical stretching and for the formation of such a zero strain stretch laminate are described in the Weber et al. '679 patent, the Buell et al. '793 patent, and the Weber et al. '897 patent.

Further, the backsheet may be "breathable," permitting vapors to escape from the absorbent core while still preventing exudates from passing through the backsheet. It is contemplated that a backsheet that is highly breathable but substantially impervious to liquid may be desirable for certain absorbent articles. Such breathable composite materials are described in greater detail in the Lim et al. '696 patent, in PCT Application No. WO 95/16746 in the name of Cardinal et al., published on Jun. 22, 1995, and in the Curro '823 patent. Other breathable backsheets including nonwoven webs and apertured formed films are described in the Dobrin et al. '096 patent.

The size of the backsheet may be dictated by the size of the absorbent core and the exact diaper design selected. In an exemplary embodiment, the backsheet has a modified hourglass-shape extending beyond the absorbent core a minimum distance of at least about 1.3 centimeters to at least about 2.5 centimeters (about 0.5 to about 1.0 inch) around the entire diaper periphery.

The topsheet may be compliant, soft feeling, and non-irritating to the wearer's skin. Further, at least a portion of the topsheet may be liquid pervious permitting bodily liquids to readily penetrate through its thickness. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can include natural fibers, e.g., wood or cotton fibers, synthetic fibers, e.g., polymeric fibers such as polyester, polypropylene, or polyethylene fibers, or a combination of natural and synthetic fibers. The topsheet may be made of a hydrophobic material to isolate the wearer's skin from liquids in the absorbent core. Like the backsheet, at least a portion of the topsheet may be subjected to mechanical stretching to make it elongatable or drawable, in order to provide a "zero strain" stretch laminate for, for example, forming elastic side panels.

A number of manufacturing techniques may be used to manufacture the topsheet. For example, the topsheet can be formed of woven, nonwoven, spunbonded, carded, or like materials. In nonwoven topsheets, the fibers may be bound together by a thermal binding procedure or by a polymeric binder such as polyacrylate. This sheet may be substantially porous and permit a liquid to readily pass through it into the underlying absorbent core. The topsheet material may have no affinity for holding aqueous bodily liquids in the area of contact between the topsheet and the wearer's skin.

High loft nonwoven topsheets and apertured formed film topsheets may be used in absorbent articles of the present disclosure. In some exemplary embodiments, apertured formed films may be used for the topsheet because they are pervious to bodily liquids and yet non-absorbent, and they have a reduced tendency to allow liquids to pass through in a direction away from the absorbent core and thereby rewet the wearer's skin. Thus, the surface of the formed film that is in contact with the body remains dry, thereby reducing bodily soiling and creating a more comfortable feel for the wearer. The body-facing surface of the formed film topsheet can be hydrophilic, thereby helping bodily liquids transfer through the topsheet faster and diminishing the likelihood that liquid will flow off the topsheet rather than flowing into and being absorbed by the absorbent core.

The topsheet may have an elasticated aperture adapted to permit feces to pass through in a direction away from the wearer and be unattached in a portion of the crotch region and a portion of the rear of the chassis. The topsheet may be fully or partially elasticized or may be foreshortened to provide a void space between the topsheet and the non-removable core component. Exemplary structures including elasticized or foreshortened topsheets are described in more detail in the DesMarais et al. '536 patent, in the Freeland '147 patent, in the Allen et al. '416 patent, and in the Freeland et al. '775 patent.

The topsheet and the backsheet may be joined together in any suitable manner. As used herein, the term "joined" encompasses configurations wherein the topsheet is directly joined to the backsheet by affixing the topsheet directly to the backsheet, and configurations wherein the topsheet is indirectly joined to the backsheet by affixing the topsheet to intermediate members which in turn are affixed to the backsheet. In an exemplary embodiment, the topsheet and the backsheet are affixed directly to each other in the absorbent article's periphery by attachment means (not shown) such as an adhesive or any other attachment means known in the art. For example, a uniform continuous layer of adhesive, a patterned layer of adhesive, or an array of separate lines or spots of adhesive can be used to affix the topsheet to the backsheet. The topsheet may also be adhered to the absorbent core.

Furthermore, it is contemplated that a suitable absorbent core structure without a topsheet could be used to provide desirable results, such as comfort and absorbency, as well as simplicity in manufacturing and material cost savings. For example, the body-side surface of the absorbent core could be made of liquid pervious, soft, compliant, non-irritating materials, thereby making a separate topsheet unnecessary. Such an absorbent core could be used in combination with a backsheet to provide the desired comfort and absorbency in an absorbent article.

Fastening means, such as tape tab fasteners 65, may be disposed in the waistband region 63 of the diaper for holding the diaper on the wearer. The waistband region is generally considered to be that portion of the diaper extending from the waist end edge of the diaper to about the laterally extending margin of the absorbent core. The tape tab fasteners depicted are representative, only, and the fastening means can be any of those well known in the art, such as the fastening tape disclosed in the Buell '594 patent, mechanical fasteners, hook and loop fasteners, zippers, buttons, and the like. These tape tab fasteners or other diaper fastening means may be applied near the corners of the diaper.

The absorbent article may have an "open" chassis configuration, as shown in FIG. 1, in which the chassis is adapted to be fastened together about the lower torso of a wearer by the fastening means. Suitable non-limiting examples of an open chassis include the disposable diaper embodiments described in the Buell '092 patent and in the LaVon et al. '500 patent.

An open chassis may be at least partially pre-fastened prior to its application onto the wearer. For example, articles capable of being pre-fastened and then applied in a pull-on fashion include those described in the Kline et al. '097 patent and in the Kline et al. '098 patent. In certain embodiments, the article may require a subsequent fastening step to adjust the size of, or the tension in, the waist circumference of the article once the article has been applied over the wearer's lower torso. For example, articles having such two-step fastening/tensioning systems include those described in currently pending U.S. application Ser. No. 09/994,191 for An Absorbent Article Fastening Device, filed Nov. 26, 2001 in the name of Magee et al.

Alternatively, the absorbent article may have a "closed" chassis configuration, such as that of a pull-on pant-type diaper or training pant, in which the chassis is adapted to be pulled on over the legs and lower torso of the wearer without any additional fastening steps. Suitable non-limiting examples of a closed system include the disposable diapers and training pants described in the Buell '234 patent and in the Ashton '487 patent.

In both open and closed chassis configurations, the absorbent article may have extensible side panels 210 and elastically extensible side panels to maximize the ease of insertion and removal of the replaceable core component. Suitable non-limiting examples of disposable absorbent articles having extensible side panels are described in the Buell et al. '092 patent, in the Buell et al. '274 patent, in the Roe et al. '145 patent, in the LaVon et al. 500 patent, in the Kline et al. '545 patent, and in the Robles et al. '306 patent.

Leg elastic members 69 may be disposed adjacent to the periphery of the diaper, such as along each longitudinal edge 64 to form an elastically contractible leg cuff or side flap, so that the elastic members tend to draw and hold the diaper against the legs of the wearer. The leg elastic members may extend along a portion of the length of the diaper. Alternatively, the leg elastic members can extend the entire length of the diaper, or any other length suitable to provide an elastically contractible line. The length of the leg elastic members may be dictated by the diaper design.

A barrier leg cuff 240 including a barrier leg cuff elastic member 241 may be disposed adjacent to each longitudinal edge 64 or between the longitudinal edge and the longitudinal centerline 17 of the diaper. Suitable barrier leg cuff materials and structures are described in the Lawson '278 patent, in the Young et al. '345 patent, in the DesMarais et al. '345 patent, in the Dyer et al., '207 patent, in the Foreman '025 patent, and in the Aziz et al. '178 patent.

Additionally, waist elastic members 67 can be disposed adjacent to either the front, the back, or both of the waistband regions of the diaper to provide a waistband as well as or rather than leg cuffs. While the waistband can comprise a separate element affixed to the body of the disposable diaper, it may be an extension of other elements of the disposable diaper, such as the backsheet or the topsheet or both the backsheet and the topsheet. Disposable diapers are sometimes constructed so as to have two waistbands: a front and a rear.

A suitable waistband is disclosed in the Kievit et al. '595 patent. In one exemplary embodiment illustrated in the Kievit et al. '595 patent, elastic waist elements extend across essentially the entire lateral width of the disposable diaper. While this construction may be used in some exemplary embodiments, similar waistbands may be useful in designs wherein the elastic waist elements extend across only a portion of the lateral width of the diaper. The elastic waist elements may extend across a major portion of the lateral width of the disposable diaper.

The elastic members are secured to the diaper in an elastically contractible condition so that in a normally unrestrained configuration, the elastic members effectively contract or gather portions of the diaper. The elastic members can be secured in an elastically contractible condition in at least two ways. For example, the elastic members can be stretched and secured while the diaper is in an uncontracted condition. Alternatively, the diaper can be contracted, for example, by pleating, and the elastic members can be secured and connected to the diaper while the elastic members are in their unrelaxed or unstretched condition. A method and apparatus suitable for manufacturing a disposable diaper having elastically contractible elastic members is described in the Buell '301 patent.

In use, an open chassis version of the diaper is applied to a wearer by positioning one waistband region under the wearer's back, and drawing the remainder of the diaper between the wearer's legs so that the other waistband region is positioned across the front of the wearer. The tape-tab or other fasteners are then be secured, for example, to outwardly facing areas of the diaper, as shown in FIG. 4, for example. As can be seen in FIG. 4, the chassis forms a waist opening 13 and leg openings 15 when configured for wearing.

The Absorbent Core

In use, the disposable diapers or other absorbent articles of the present disclosure may tend to more quickly and efficiently distribute and store liquids and remain dry due to the high absorbent capacity of the absorbent core components. Disposable diapers incorporating the absorbent core components of the present disclosure can also be thinner and more flexible.

Figure 5:
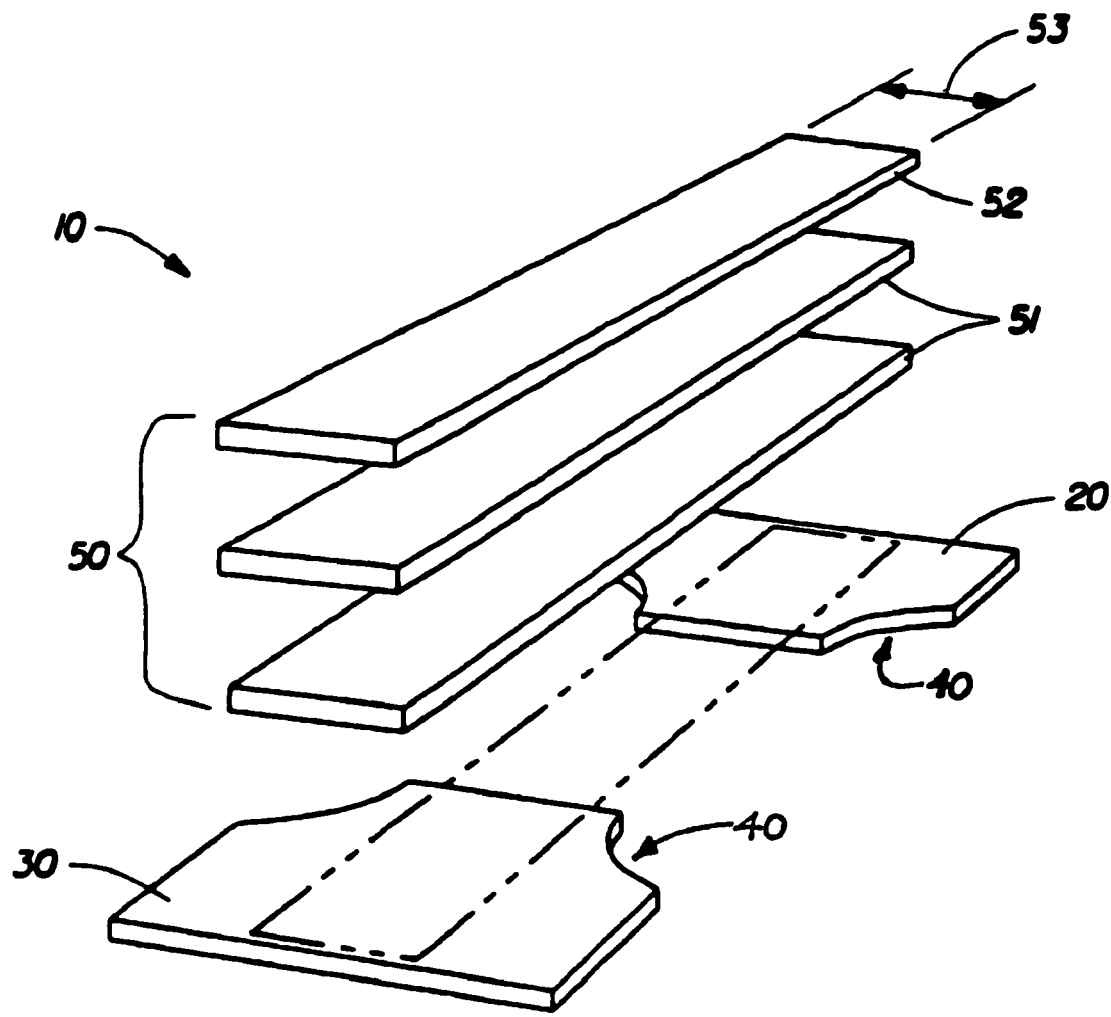
FIG. 5 is an exploded perspective view depicting the relationship between the elements of an exemplary absorbent core, with the portion of the core that faces the wearer facing upward.
Figure 6:
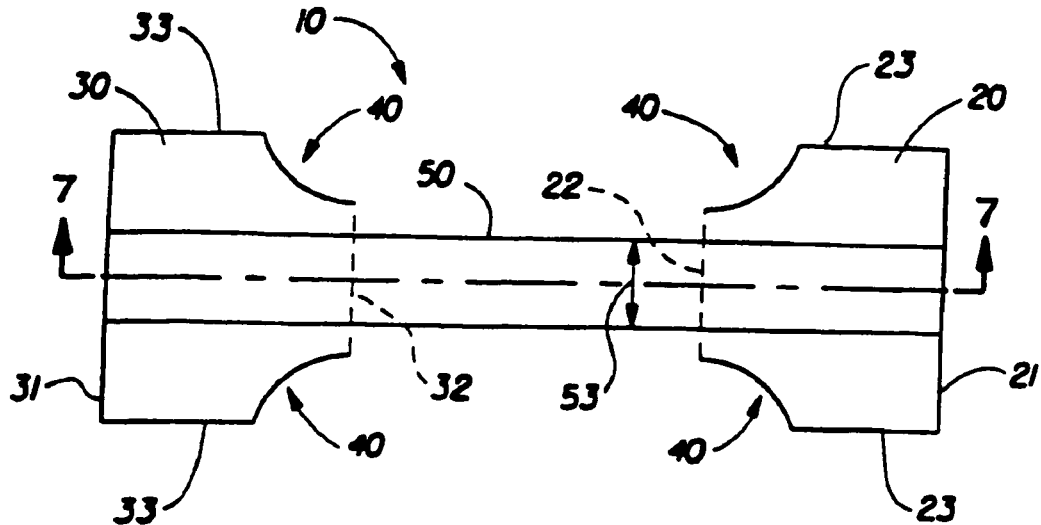
FIG. 6 shows a top plan view of an exemplary absorbent core useful in an absorbent article.

FIG. 5 shows an exploded perspective view depicting the elements of an exemplary embodiment of a shaped absorbent core 10 such as may be used in an absorbent article, for example, in a disposable diaper. FIG. 6 shows a top plan view of such a shaped absorbent core 10.

As depicted in FIG. 5 and FIG. 6, the absorbent core 10 includes a front panel 20 and a back panel 30, both made of absorbent material, for example, material suitable for liquid storage/redistribution. The front panel has an outer front end 21, an inner front end 22, and a pair of sides 23. Similarly, the back panel has an outer back end 31, an inner back end 32, and a pair of sides 33. In this exemplary embodiment, the front and back panels, together with the center section 50, generally form an elongated hourglass shape suitable for use in a disposable diaper or similar absorbent article.

Since the center section 50 and the front panel 20 and the back panel 30 are discrete absorbent core components, the center section 50 may be non-removable, while the front panel 20 or the back panel 30, or both, may be removable from the diaper 60. Thus, when the front panel 20 or the back panel 30 becomes saturated with water and/or bodily discharges, such as urine, it can be removed and replaced with a fresh panel for continued use of the absorbent article.

The center section may be generally rectilinear. The term "generally rectilinear" refers to the center section having a generally constant width along its length. In general, however, the center section may have a varying width along its length. The center section may extend from about the outer front end 21 of the front panel, to about the outer back end 31 of the back panel, as shown in FIG. 6. In use, however, the center section need only be in capillary liquid communication with the front and back panels, such as by overlapping in a layered relationship, and may not extend to the outer front end or the outer back end.

In an exemplary embodiment, the width 53 of the center section is suitable for comfortably fitting within the crotch area of the wearer when the absorbent core is incorporated into an absorbent article, such as a disposable diaper. The length of the generally rectilinear center section may be varied to provide a suitable fit for various wearer sizes.

In a generally flat, unfolded state, the front panel and the back panel are disposed such that the inner front end 22 of the front panel is opposed to and spaced from the inner back end 32 of the back panel as shown in FIG. 5 and FIG. 6. The distance between the front and back panels may be varied as necessary. In general, the distance will increase as the crotch length increases with the size of the absorbent article. The front panel generally lies in the front waist region, with the outer front end 21 being generally near the front waist end edge and the inner front end 22 lying in the crotch region. Similarly, the back panel lies in the back waist region, with the outer back end 31 being generally near the back waist end edge and the inner back end 32 lying in the crotch region. In some exemplary embodiments, the back panel 30 is longer than the front panel 20. Such a configuration may lend itself to a better fit when the absorbent core is used in a disposable diaper.

As shown in FIG. 2, FIG. 3, FIG. 5, and FIG. 6, the front panel 20 may have cut-out areas 40 at the intersection of the sides 23 and the inner front end 22 and the back panel 30 may have cut-out areas 40 at the intersection of the sides 33 and the inner back end 32. The cut-out areas, or notched portions, join the sides and the inner ends such that the resulting widths of the inner ends 22 and 32 are narrower than those of the outer ends 21 and 31, respectively and, as shown in the figures, approach the width 53 of the center section, which is suitable for comfortably fitting within the crotch area of the wearer when the absorbent core is incorporated into an absorbent article, as stated above. The term "notched" refers to a shape in which, instead of a side and an end meeting generally at a right angle, some amount of material is removed from the corner to produce an additional edge portion joining the side and the end. The additional edge portion of the cut-out areas may be generally straight, but in an exemplary embodiment it is generally arcuate, as depicted in FIG. 6. It is also contemplated that the cut-out areas may have generally straight sides, with the non-limiting example resulting in a back panel or a front panel being substantially trapezoidal in shape.

Figure 12:
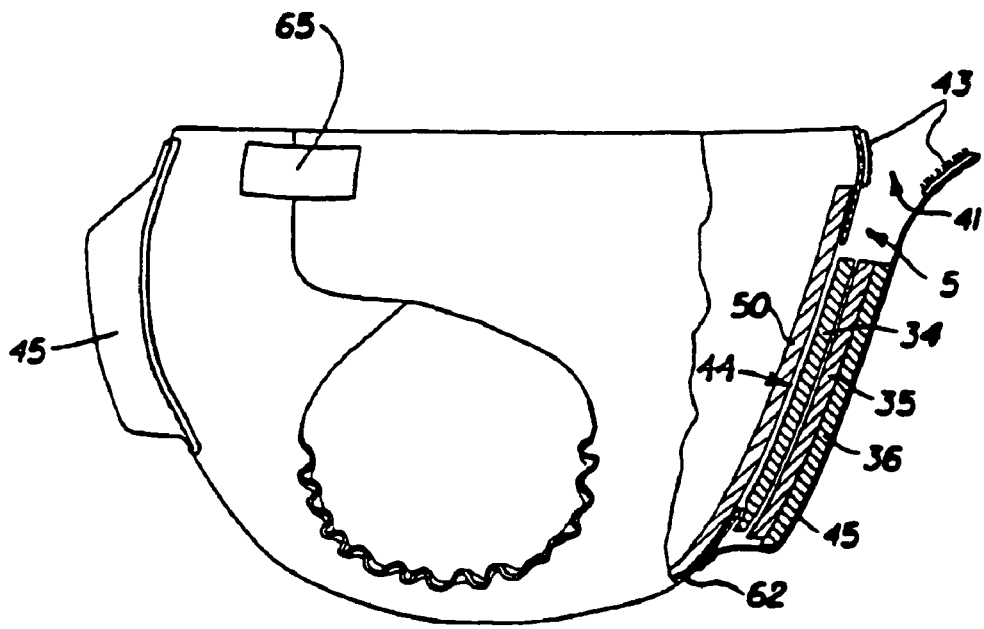
FIG. 12 is a side view, showing in partial cross-section, another alternative exemplary absorbent article.

The center section may include multiple layers of absorbent material, each having individual liquid acquisition, acquisition/distribution or storage/redistribution characteristics, as well as individual shape, width, length and thickness characteristics. The number and placement of absorbent layers of the center section may be varied to achieve certain characteristics such as thinness, softness, flexibility, or beneficial liquid acquisition, distribution, and storage rates. For example, the layers of the center section need not extend from one waist region through the crotch to the opposing waist region. In particular, the center section may include an absorbent layer extending from one waist region into the crotch region, where it ends, and another absorbent layer extending from the opposing waist region into and ending in the crotch region. The number of absorbent layers of the front and back panels may also be varied to achieve certain characteristics such as beneficial liquid acquisition and distribution rates, as well as capacity and storage rates, and wearer comfort. For example, in FIG. 3, the absorbent core is shown with the center section 50 and the front and back panels 20 and 30 each having a single absorbent layer. However, the center section has three absorbent layers in the exemplary embodiments shown in FIG. 2 and FIG. 5, with two absorbent layers designated 51 and one absorbent layer designated 52. Also, the back panel is shown in FIG. 12 as a core component made up of back panel absorbent layers 34, 35, and 36.

Figure 7:
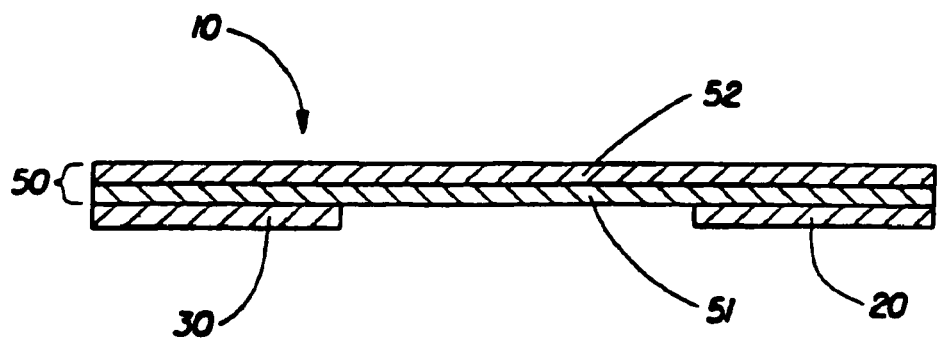
FIG. 7 is a sectional view of an exemplary absorbent core similar to that shown in FIG. 6, taken along line 7-7, with the portion of the core that faces the wearer oriented upward.

In the exemplary embodiment shown in cross section in FIG. 7 and corresponding to the general top view of FIG. 6, one upper absorbent layer 52 and one lower absorbent layer 51 are both placed over front and back panels 20 and 30, resulting in a thin, flexible absorbent core. The term "over" refers to the surface of the absorbent core corresponding to the wearer's body when used in an absorbent article such as a disposable diaper, i.e., the body-facing surface. It is noted, however, that FIG. 7 is representative of only one exemplary embodiment and it may be beneficial to place the absorbent layers 51 or 52 under the front and back panels 20 and 30. The term "under" refers to the surface of the absorbent core corresponding to the garment side when used in an absorbent article such as a catamenial pad or disposable diaper, i.e., the garment-facing surface. It should also be understood that the term "upper" refers to the absorbent layer of the absorbent core which is nearest to and faces the article topsheet; conversely, the term "lower" refers to the absorbent layer of the absorbent core which is nearest to and faces the article backsheet.

Figure 8:
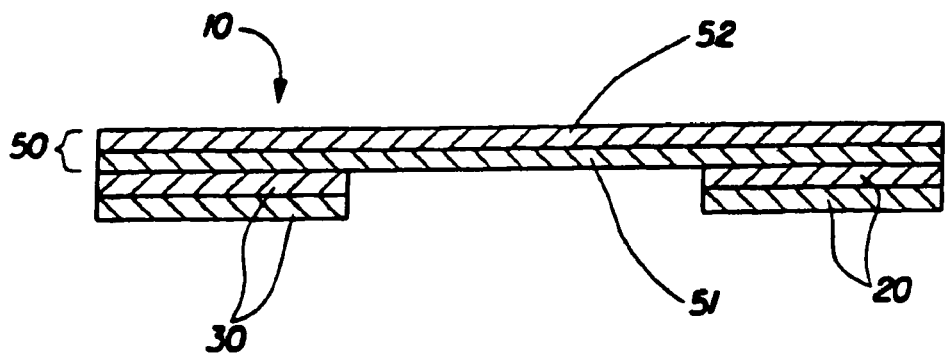
FIG. 8 shows a sectional view of another alternative exemplary absorbent core, with the portion of the core that faces the wearer oriented upward.
Figure 9:
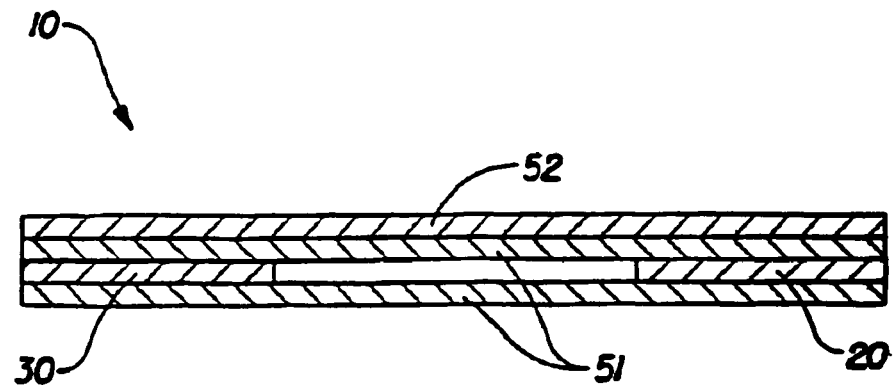
FIG. 9 shows a section view of another alternative exemplary absorbent core, with the portion of the core that faces the wearer oriented upward.
Figure 10:
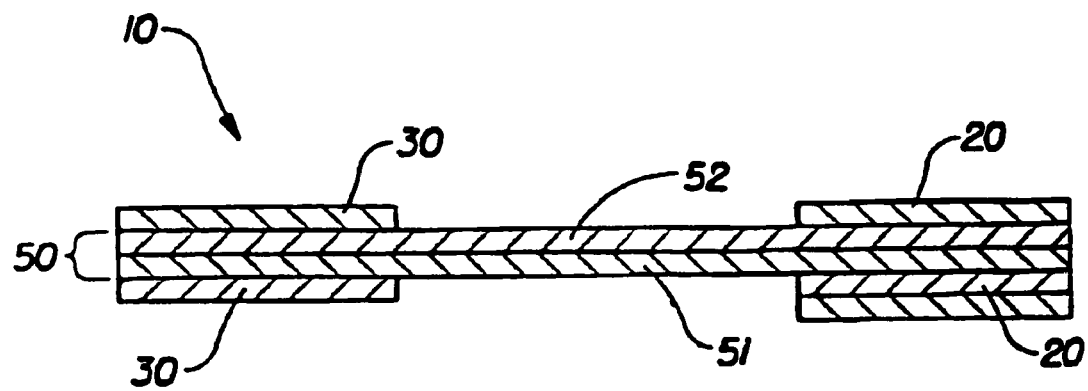
FIG. 10 shows a section view of another alternative exemplary absorbent core, with the portion of the core that faces the wearer oriented upward.

Other arrangements of the absorbent layers of the center section and the front and back panels are also possible. For example, FIG. 8 shows in cross-section an additional exemplary embodiment corresponding to the general top view of FIG. 5, in which two absorbent layers of front and back panels 20 and 30 are placed under the center section 50. As shown in the Weber et al. '602 patent and in FIG. 9, an alternative embodiment may have a center section 50 having two absorbent layers 51, one placed over front and back panels 20 and 30, and one placed under the front and back panels, thereby sandwiching the front and back panels between absorbent layers of the center section. As another example, as shown in the Weber et al. '602 patent and in FIG. 10, the front and back panels 20 and 30 may have two absorbent layers, with one absorbent layer placed over the center section 50 and one absorbent layer placed under the center section 50, thereby sandwiching the ends of the center section between absorbent layers of the front and back panels.

As shown in FIG. 7, the uppermost absorbent layer 52 is generally on the side corresponding to the body side of an absorbent article, such as a disposable diaper. Therefore, the uppermost absorbent layer 52 is generally in capillary liquid communication with topsheet 61 of the disposable diaper, thereby acting to quickly acquire and partition bodily exudates away from the wearer's body to the generally more absorptive lower absorbent layers 51 and to the front and back panels 20 and 30. Adhesive bonding of the uppermost absorbent layer 52 to the topsheet 61 may enhance the capillary liquid communication by providing interfacial bonding and preventing topsheet separation from impeding liquid flow.

The Absorbent Core Materials

The components or members of the absorbent core may include laminates or combinations of several sheets or webs of the requisite types of materials. In general, each absorbent core component or member may be made of any absorbent material or combination of materials having enough structural integrity to be handled as a discrete unit.

For example, in order for a low absorbency core component, which may also be non-removable, such as the center section, to function in a certain way, the structural integrity of the component may be maintained in order to maintain its ability to transport liquid from the front of the absorbent article to the rear of the absorbent article and/or from the crotch region of the absorbent article to the waist regions. If an absorbent layer of the low absorbency core component is torn or fractured, the liquid transport and capillary liquid communication with the replaceable core component can be interrupted. Therefore, when dry, the absorbent layer or layers of the low absorbency core component may have a tensile strength to break of greater than about 200 grams force or greater than about 400 grams force or greater than about 1000 grams force. When completely wetted, the absorbent layer or layers of the low absorbency core component may have a tensile strength to break of greater than about 100 grams force or greater than about 200 grams force or greater than about 400 grams force. The structural integrity can also be achieved by affixing a carrier layer having the required tensile to break characteristics to the low absorbency core component or to the absorbent layer along its major surfaces or, alternatively, by wrapping the non-removable core component or the absorbent layer in the carrier layer.

Typical materials known in the art may be used for the absorbent core components and/or members, such as fibrous nonwoven materials, fibrous air-laid materials, fibrous wet-laid web materials, and combinations of fibrous materials having absorbent gelling materials dispersed upon or within the fibrous structure. If necessary, such absorbent core components or members may be formed into a packet having the fibrous materials substantially enveloped by a liquid pervious web that provides the structural integrity for the removal and replacement into the absorbent article. An exemplary form of a non-woven fibrous absorbent structure that may be utilized is constructed from hydrophilic chemically stiffened cellulosic fibers, as taught in the Lash '728 patent and the Young et al. '345 patent, as well as in the Seger et al. '416 patent.

Absorbent materials for use as absorbent core components or members may also be foam-based. For example, a component of the absorbent core may include a foam material in the form of a sheet or a plurality of foam pieces or particles, which may be adhesively bonded together or which may simply be constrained into an unbonded aggregate held together by an overwrapping of envelope tissue or by means of the topsheet and backsheet of the absorbent article. Particularly suitable absorbent foams for absorbent articles such as diapers have been made from High Internal Phase Emulsions, hereafter referred to as "HIPE". See, for example, the DesMarais et al. '345 patent, the DesMarais et al. '224 patent, and the Stone et al. '179 patent.

The absorbent core of the absorbent articles described herein can also include a combination of conventional elements or materials and one or more foam absorbent structures. For example, the absorbent articles may utilize an absorbent core which includes a combination, e.g., an airlaid mixture, of particles or pieces of the foam absorbent structures and conventional absorbent materials such as wood pulp or other cellulosic fibers and/or particles or fibers of polymeric gelling agents.

Besides acquiring bodily liquids rapidly, the absorbent acquisition member should give up this liquid efficiently to the liquid acquisition/distribution or storage/redistribution members. This liquid transfer function of the acquisition member may be of particular importance because the acquisition member must have sufficient capillary suction to substantially drain the liquid from the topsheet and yet not exhibit excessive liquid retention, which would make it difficult for the underlying absorbent layer to desorb the acquisition member.

In particular, the liquid acquisition member may have a suitable capillary desorption pressure relative to the absorption pressure of other absorbent core members, especially those intended for liquid storage. If the liquid acquisition member of the absorbent article holds the acquired liquid too tenaciously, this may inhibit the ability of these other members to partition liquid away and can cause the acquisition member to remain so heavily loaded with liquid that the absorbent article may be more susceptible to leaking.

This principle, according to which the relationship of the capillary absorption pressure of one absorbent element and the capillary desorption pressure of another absorbent element defines the liquid flow, liquid transfer, and capillary liquid communication characteristics of the absorbent article, is that of a capillary cascade. For example, the wearer-facing layer of the absorbent article, e.g., a topsheet, is liquid pervious and has particular capillary absorption and desorption pressures. The capillary desorption pressure of this topsheet may be less than the capillary absorption pressure of the non-removable core component and, specifically, less than the capillary absorption pressure of the uppermost absorbent layer of the non-removable core component, with which the topsheet will be in contact. It may also be that the capillary absorption pressure of an intermediate or lowermost absorbent layer of the non-removable core component is greater than the capillary desorption pressure of the topsheet. In addition, it may be that the absorption pressure of a lower absorbent layer of the non-removable component be greater than the capillary desorption pressure of the uppermost absorbent layer of the non-removable core component. Furthermore, it may be that the capillary absorption pressure of the storage/redistribution member of the replaceable core component be greater than the capillary desorption pressure of the absorbent layer of the non-removable core component in contact with the replaceable core component.

In addition to having to overcome the capillary desorption pressure of an adjacent absorbent structure, an absorbent layer may need to overcome the difference in vertical height between a source of liquid and the portion of the absorbent layer to which it is desired to move the liquid by capillary transport. The magnitude of this vertical head may be on the order of 15 cm to 20 cm in some embodiments, in which liquid is moved from the lower portion of the crotch region to the upper waist region of an absorbent article worn by a standing wearer, is moved from the front portion to the back panel of an absorbent article worn by a wearer lying in a face-down posture, or is moved from the back portion to the front panel of an absorbent article worn by a wearer lying in a face-up posture.

The liquid acquisition/distribution member may include materials similar to those used in the acquisition member, but may have more distributive characteristics. Since discharged aqueous bodily liquid, e.g., urine, is frequently discharged in gushes, the acquisition/distribution member must be able to quickly acquire this liquid and must also transport the liquid by wicking or another mechanism from the point of initial liquid loading to other parts of the acquisition/distribution member for eventual desorption to the adjacent liquid storage/redistribution member. Thus, such materials may have a greater degree of distributive capacity than the acquisition member materials, such that bodily exudates may be efficiently transported from the acquisition zone to the storage members of the absorbent core.

In order to provide the above-described functionality in some exemplary embodiments, compositions for the absorbent core may be selected such that the acquisition side of the absorbent layer is comparatively free of small, high surface area fibers which provide good distributive and storage characteristics but less than optimal acquisition characteristics and such that the distributive side of the absorbent layer has a comparatively higher proportion of such small, high surface area fibers so as to provide greater distribution characteristics. In some embodiments, the acquisition area may have both a relatively lower average density and lower average basis weight per unit area than the distribution area to establish the capillarity force gradient between them. Also, in foam absorbent core structures, cell sizes and hole sizes are parameters that can impact a number of important mechanical and performance features of the foams, including their fluid wicking properties and the capillary pressure that is developed within the foam structure, as described in the Stone '179 patent.

In some embodiments, it may be desirable to have a "biased" absorbent core structure, wherein a portion adjacent to one surface is capable of rapidly acquiring a liquid with minimal dispersion, while a portion adjacent to an opposing surface is capable of rapidly dispersing a liquid with lesser acquisition capability. When oriented in an absorbent article such that the "acquisition side" is oriented toward the wearer and the "distribution side" is oriented away from the wearer, a "down and out" functionality is provided, whereby liquid is rapidly acquired into the absorbent core structure with minimal dispersion on its wearer-facing side and is rapidly distributed throughout the portion of the absorbent core structure on its garment-facing side. This functionality allows the maintenance of a clean and dry visible and tactile impression of the absorbent core structure, and hence the absorbent article, while effectively utilizing the absorptive capacity of the regions of the absorbent article oriented away from the wearer.

Optionally, a liquid pervious sheet, e.g., a tissue sheet, or a scrim layer is positioned between the acquisition/distribution member and the storage/redistribution member to maintain the physical integrity of the acquisition/distribution member during processing and/or use. This liquid pervious sheet can envelop all or part of the acquisition/distribution member, or simply be positioned as described above, without necessarily enveloping the acquisition/distribution member. In embodiments in which the center section of the absorbent core includes the acquisition and acquisition/distribution members and is placed over or under a replaceable absorbent core component or absorbent insert including the storage/redistribution member, such as a back panel, a single such liquid pervious sheet may suffice. Alternatively, in embodiments in which absorbent layers of the center section sandwich the replaceable absorbent core component or absorbent insert, two or more such liquid pervious sheets may be positioned to separate the absorbent layers of the center section and the replaceable core component. These multiple liquid pervious sheets may be described as forming a surface of or lining the openable chassis pocket formed by and between the sandwiching absorbent layers of the center section. Similarly, in embodiments in which absorbent layers of a replaceable absorbent core component or absorbent insert sandwich an end of the center section, two or more such liquid pervious sheets may be positioned to separate the absorbent layers of the center section and the replaceable core component. In the latter embodiment, the multiple liquid pervious sheets may be described as forming a surface of or lining the two-part openable chassis pocket into which the replaceable absorbent core component or absorbent insert is inserted and which is formed by and between the topsheet and the center section and by and between the center section and the backsheet, respectively.

An absorbent core may include at least one absorbent core component including a liquid storage/redistribution member and may include two such components, e.g., in the form of front and back panels. Each absorbent core component having a liquid storage/redistribution member acts to store bodily exudates away from the wearer's body, so as to leave the wearer with a feeling of dryness and to prevent leakage. The absorbent core component having the liquid storage/redistribution member is maintained in capillary liquid communication with the acquisition and/or acquisition/distribution member(s), such that urine or other aqueous bodily liquid can be desorbed from the acquisition and/or acquisition/distribution member(s) and be absorbed by the liquid storage/redistribution member.

The storage/redistribution member may include a member or members having primarily liquid storage characteristics. Such a storage member may have limited transport and wicking capabilities but high storage or retention capacity, and rely upon a liquid distribution member to distribute incoming liquid over a larger area of the storage/redistribution member.

The absorbent articles may be constructed such that when liquid is deposited in the article, the liquid is quickly absorbed and transported from the non-removable core component to the replaceable core component. In order to minimize the bulk of the absorbent article and to maximize the benefits of skin health and dryness, the non-removable core component may have a liquid storage capacity that is low relative to the total capacity of the absorbent core, i.e., relative to the total of the summed capacities of the non-removable and replaceable core components. Furthermore, it may be desirable to remove the majority of the liquid deposited in the article by removing the replaceable core component and replacing it with a fresh dry component. Therefore, the liquid absorptive capacity of the replaceable core component may be significantly greater than the liquid absorptive capacity of the non-removable core component. The liquid absorptive capacity of the replaceable core component may be at least about 1.5 times as great as the liquid absorptive capacity of the non-removable core component, at least about 2 times as great, or at least about 4 times as great as the liquid absorptive capacity of the non-removable core component.

The replaceable core component may include an absorbent layer including an acquisition material, which may be the same material as the uppermost absorbent layer of the non-removable core component. This acquisition material may form a portion of the outer surface of the replaceable core component or, alternatively, the acquisition material may be disposed under another layer of liquid pervious material. The absorbent layer of the replaceable core component including the acquisition material may be disposed in capillary liquid communication with the topsheet or in capillary liquid communication with a portion of the non-removable core component.

In some embodiments, the replaceable core component may include an absorbent layer including a distribution material, which may be the same material as that in an intermediate or a lower absorbent layer of the non-removable core component. This distribution material may form a portion of the outer surface of the replaceable core component or, alternatively, the distribution material may be disposed under another layer of liquid pervious material. The distribution material may be disposed adjacent to either the wearer-facing surface of the replaceable core component or the garment-facing surface of the replaceable core component, or both. Furthermore, the distribution material may be in capillary liquid communication with the topsheet or in capillary liquid communication with a portion of the non-removable core component.

The replaceable core component may include multiple absorbent layers or pieces, including at least a liquid storage member and/or a liquid storage/redistribution member. The replaceable core component may also have one or more layers forming a packet to partially or completely contain the absorbent layer or layers. The packet layers may include liquid pervious materials, liquid impervious materials, or combinations thereof, and at least a portion of one of the packet layers forming the outer surface of the replaceable core component must have a liquid pervious region. In some embodiments, an outer surface of the replaceable core component may be formed by an acquisition member, a distribution member, or an acquisition/distribution member disposed in such a way as to contain the absorbent layer or layers in which the liquid storage member and/or the liquid storage/redistribution member is included. Also, in some embodiments, these additional absorbent members may be disposed between the packet layers forming the outer surface of the replaceable core component and the storage or storage/redistribution member.

In summary, the absorbent core 10 includes a plurality of discrete components, each component having distinct liquid acquisition, acquisition/distribution, or storage/redistribution characteristics. The absorbent core components may be positioned relative to one another in a wide variety of configurations to place each of the acquisition, acquisition/distribution, and storage/redistribution members in capillary liquid communication with an adjacent member or members. There is no particular criticality with respect to the positional relationship of the acquisition/distribution member and the liquid storage/redistribution member within the absorbent core for these members to be in effective capillary liquid communication with each other and for each member to be capable of effectively holding and/or transporting the amount of aqueous bodily liquid that is expected to be discharged into the absorbent article. It should be noted that the various structures of absorbent articles may or may not be generally planar in nature, and may be shaped or profiled in any desired configuration.

The Structure Allowing Removal and Replacement of Core Components

As shown in FIG. 2, FIG. 3, and FIG. 4, the backsheet 62 of some exemplary embodiments of an absorbent article may have an aperture 44 in the general proximity of the front panel 20 or rear panel 30, or both.

As shown in FIG. 4, the aperture 44 provides access into what may be described as an openable chassis pocket 5, with a removable absorbent core component, for example, the back panel 30, being disposed inside the openable chassis pocket when the diaper is being worn, and being removable from and replaceable into the openable chassis pocket through the aperture. For example, after the removal of a saturated back panel, a fresh, unused absorbent core component may be reinserted through the aperture. A flap 42 may be provided to cover the aperture. The material used for the backsheet may be used for the flap as well. When the disposable diaper is being worn, the flap may be secured over the aperture by suitable fasteners 43, such as VELCRO strips or adhesive strips (not shown). For example, FIG. 4 shows the flap in the closed position over the aperture adjacent to the front panel 20 (shown in FIG. 3). The flap may be sealed with releasable adhesive, thereby providing for liquid impermeability when closed, but allowing for multiple openings and closings.

In the exemplary embodiment shown in FIG. 3 and FIG. 4, the back panel 30 is disposed under the center section, as in the description of FIG. 7, above, and the openable chassis pocket 5 is formed by and between the center section 50 and the backsheet 62. In other exemplary embodiments, in which the center section and the removable core component or components are arranged differently, the openable chassis pocket may be formed by and between different components and layers. For example, in an embodiment in which the back panel is disposed above the center section, the openable chassis pocket may be formed by and between a topsheet and the center section. Similarly, when the back panel is sandwiched between absorbent layers of the center section, as in FIG. 9, the openable chassis pocket may be formed by and between the sandwiching absorbent layers of the center section. Also, when the center section is sandwiched between absorbent layers of the back panel, as in FIG. 10, the openable chassis pocket may be formed in two parts, by and between the topsheet and the center section and by and between the center section and the backsheet, respectively.

In general, the front panel, the back panel, and the corresponding apertures and flaps are substantially similar, but need not be. In an alternative exemplary embodiment, only one aperture and flap may be included, for example, for access to the back panel, without providing a similar aperture for access to the front panel.

Figure 11:
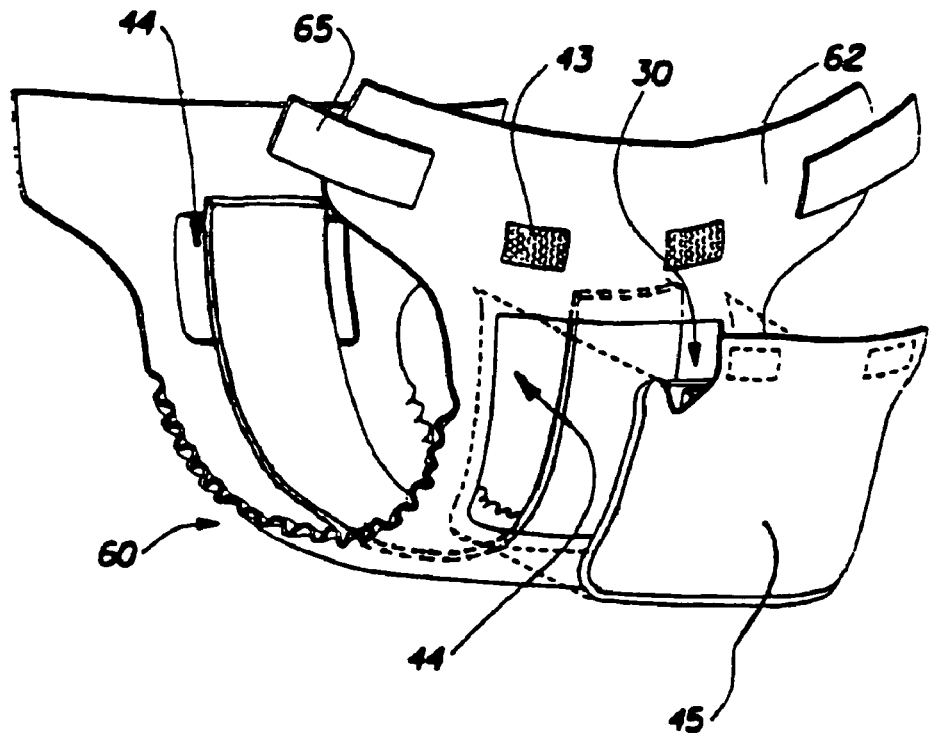
FIG. 11 is an exploded, perspective, partially segmented illustration of an alternative exemplary absorbent article.

Alternatively, as shown in FIG. 11 and FIG. 12, a backsheet pocket sheet 45 may be affixed on the garment-facing surface of the backsheet adjacent to the aperture 44 to form an openable chassis pocket 5 between the backsheet pocket sheet and the backsheet. In these embodiments, a removable and replaceable core component, such as back panel 30, may be disposed outside, relative to the aperture, and a core component that remains in the absorbent article, i.e., a non-removable core component, such as center section 50, may be disposed inside, relative to the aperture, such that the aperture allows capillary liquid communication between the replaceable core component and the non-removable core component.

The openable chassis pocket 5 formed by the backsheet pocket sheet 45 may have its openable end 41 longitudinally nearest the adjacent waist end edge. The openable chassis pocket may be reclosable and may be resealable, and may be positioned so that the back panel is urged into capillary liquid communication with the center section. The backsheet pocket sheet may be resilient and pliable, and forms a substantially liquid impervious barrier over the aperture, functionally becoming an extension of the backsheet when the openable chassis pocket is closed.

The back panel is shown in FIG. 12 as a core component made up of individual back panel absorbent layers 34, 35, and 36. In such an embodiment, as one back panel absorbent layer, e.g., the uppermost back panel absorbent layer 34, becomes saturated with bodily discharge or other liquids it may be removed, thereby exposing an adjacent prepositioned back panel absorbent layer, e.g., the adjacent back panel absorbent layer 35.

Figure 13:
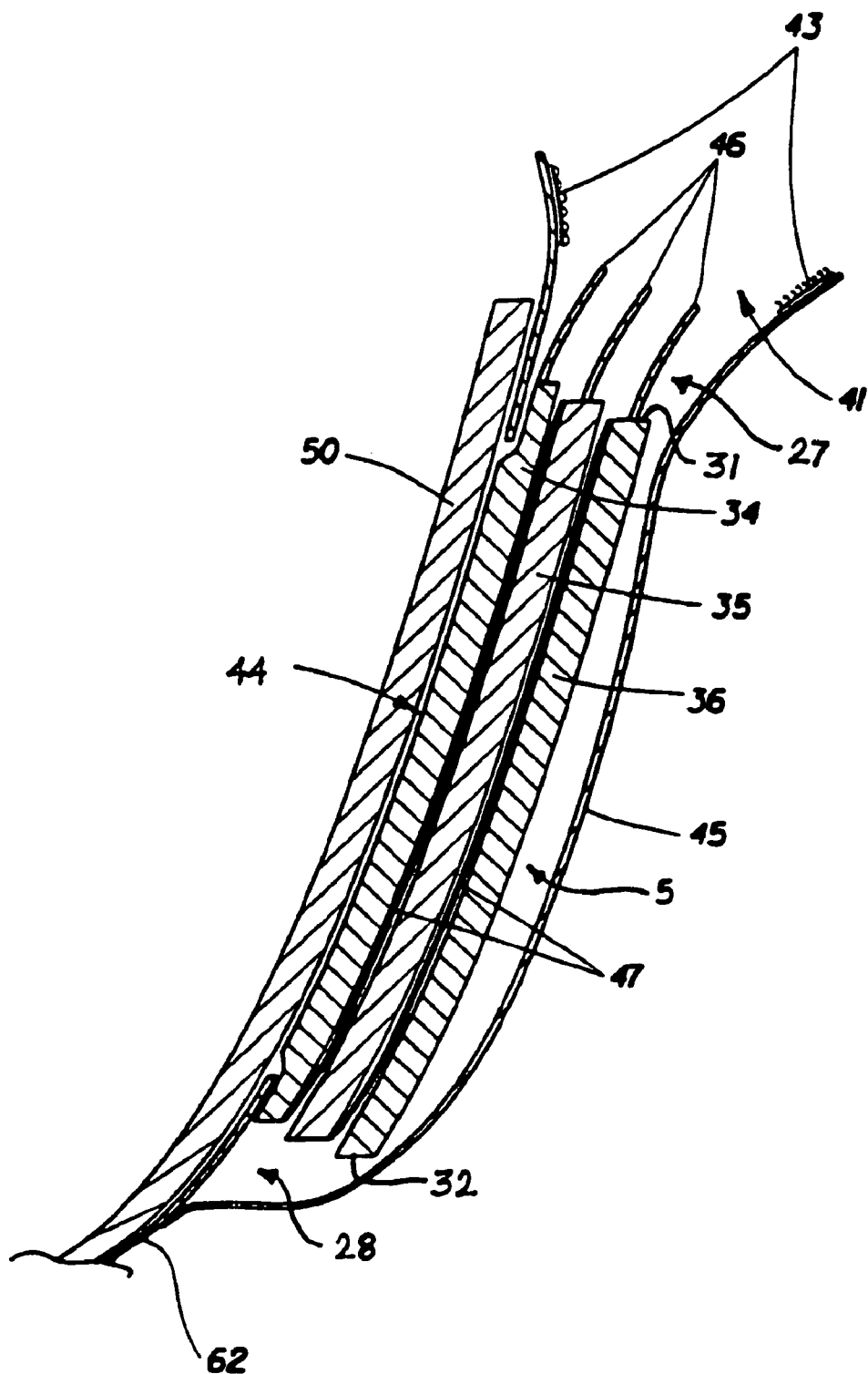
FIG. 13 is a cross-section illustration of a portion of an exemplary absorbent article having an opening through the backsheet.

FIG. 13 shows an exemplary embodiment of the arrangement of the back panel 30, again showing representative back panel absorbent layers 34, 35, and 36 in a layered relationship adjacent to the aperture 44 and in capillary liquid communication with the center section 50. Removal of the back panel absorbent layers through the openable end 41 of the openable chassis pocket 5 may be facilitated by the use of pull tabs 46, which may be of any type known in the art, such as a strip of plastic film adhered to each back panel absorbent layer.

Additionally, the back panel absorbent layers may be separated from one another by a liquid impervious blocking layer 47 so that adjacent back panel absorbent layers are not in capillary liquid communication with each other. The blocking layer 47 may be any liquid impervious polymer film, such as film suitable for use as a liquid impervious backsheet. As one back panel absorbent layer becomes saturated by absorption of liquid from the center section 50, it may be removed, thereby exposing a substantially dry, fresh adjacent back panel absorbent layer for additional absorption from the center section 50. In this manner, the absorbent article may be refreshed or regenerated for a prolonged period of time without the necessity of its removal from the wearer.

Figure 14:
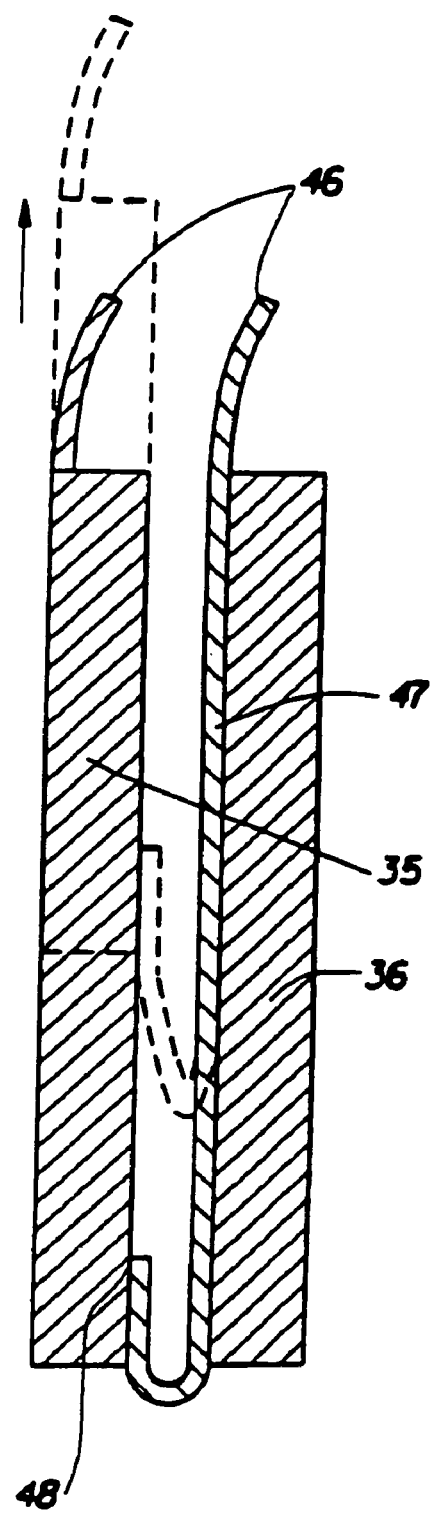
FIG. 14 is a cross-section detail of an exemplary configuration of removable and replaceable absorbent core layers.

FIG. 14 shows an exemplary arrangement of the back panel absorbent layers 35 and 36 in a layered relationship with the liquid impervious blocking layer 47 disposed to form a liquid impervious layer between them. A portion of the blocking layer may be affixed, for example at an attachment point 48, to the back panel absorbent layer being removed. As this back panel absorbent layer 35 is removed, the blocking layer 47 is removed as well, thereby leaving the adjacent back panel absorbent layer 36 in position to be urged into capillary liquid communication with the center section 50.

Figure 15:
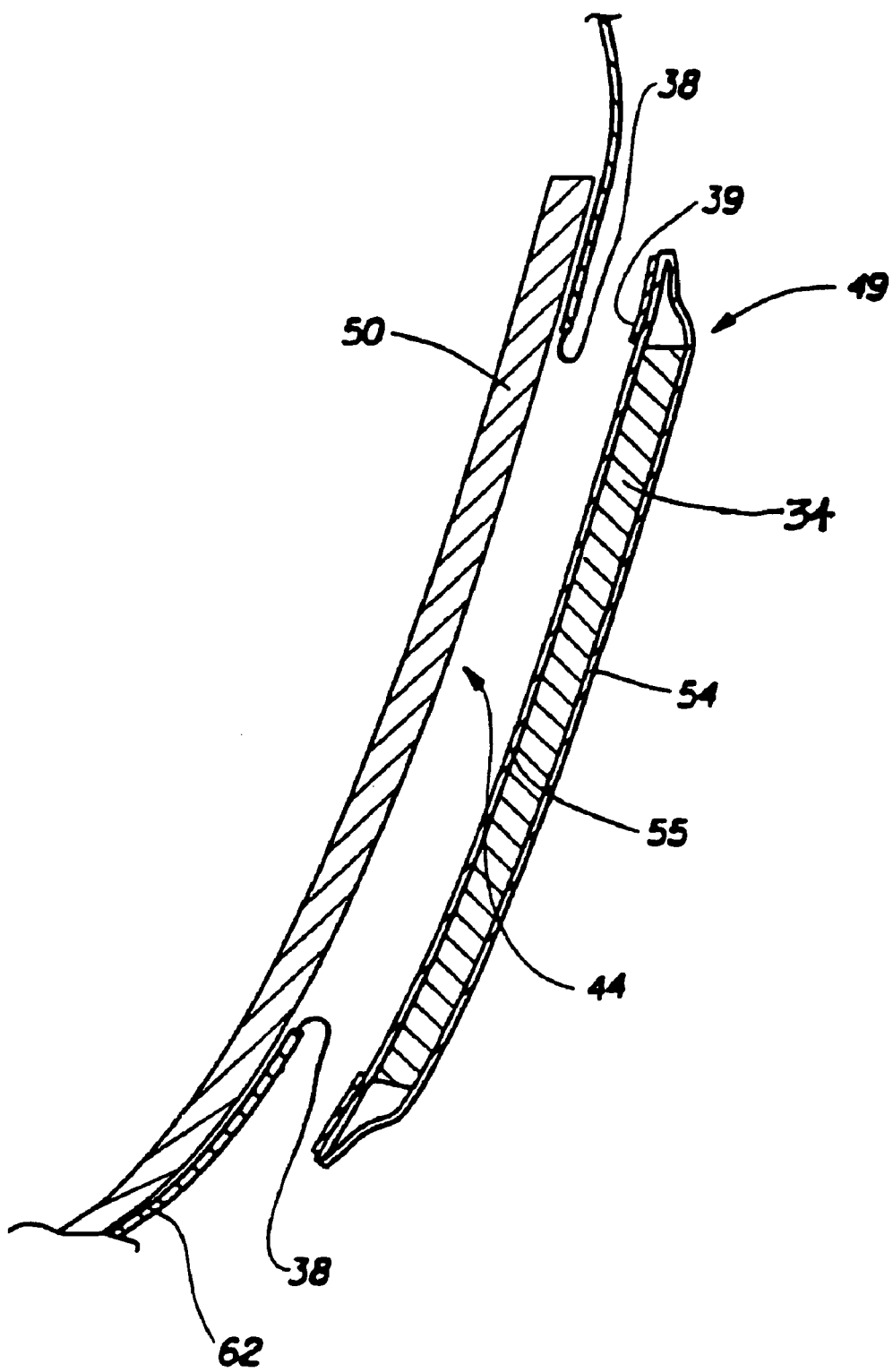
FIG. 15 is a cross-section detail of an alternative exemplary configuration of a removable and replaceable absorbent core component.

An alternative exemplary embodiment of the back panel 30 of an absorbent article is shown in cross-section in FIG. 15, in which a back panel envelope 49 is shown in position to be attached to the backsheet 62. The back panel envelope is shown as containing a single back panel absorbent layer 34 enveloped between a substantially liquid impervious layer 54 and a substantially liquid pervious layer 55, and may be releasably affixed, for example, by a suitable releasable adhesive 39 known in the art, adjacent to the perimeter 38 of the aperture 44. When such a releasably affixed back panel envelope becomes saturated due to the absorption of liquid from the center section 50, it may be removed and replaced with a fresh, dry back panel envelope 49.

Figure 16:
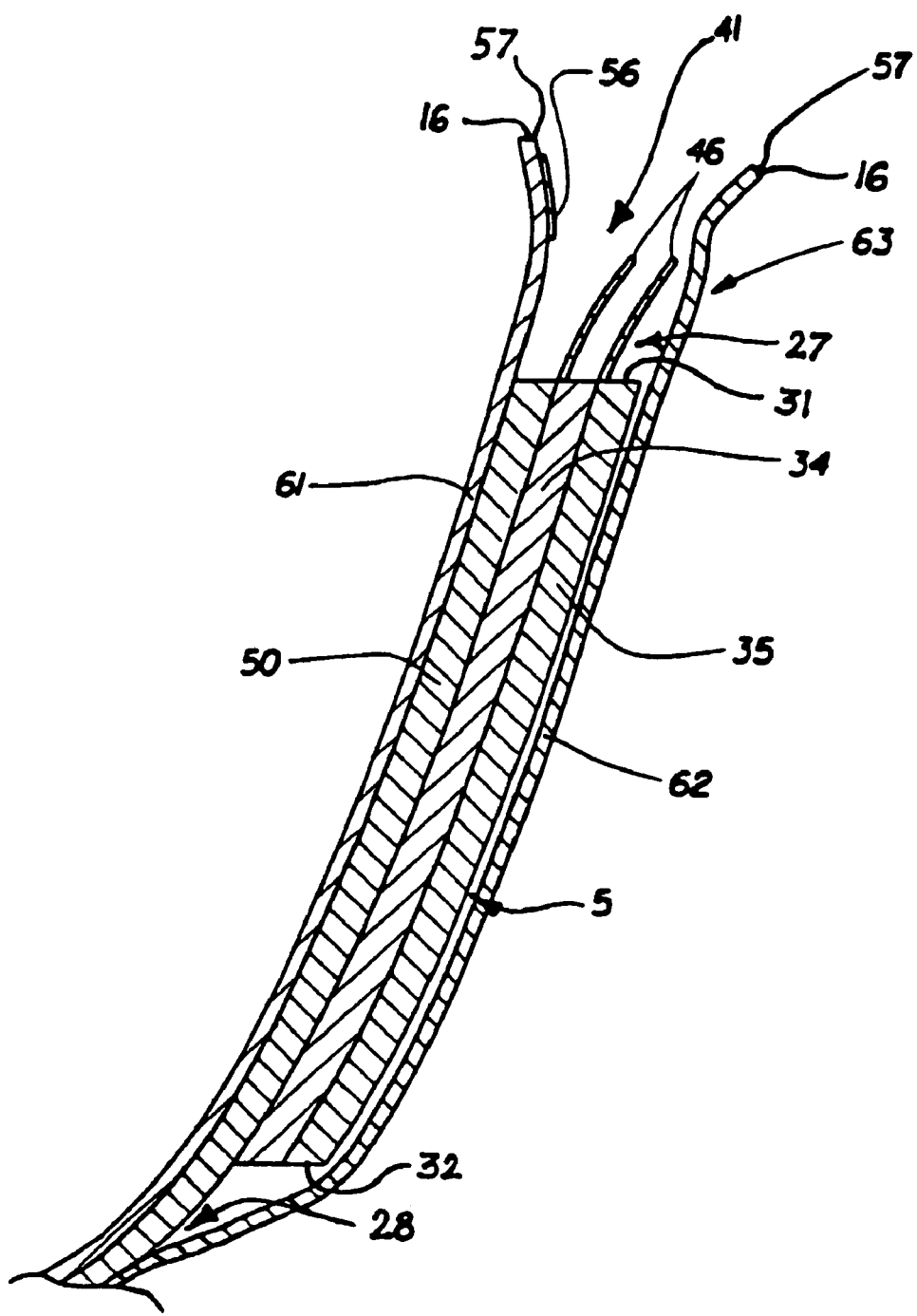
FIG. 16 is a cross-section depiction of an additional alternative exemplary configuration of removable and replaceable absorbent core layers.

In another alternative exemplary embodiment of an absorbent article shown in cross-section in FIG. 16, the openable end 41 of the openable chassis pocket 5 may be formed along a predetermined area of the periphery 57, such as along the waist end edge 16, either in the front, in the back, or both, where the topsheet 61 and the backsheet 62 are separable to provide access to the removable absorbent core component, e.g., the back panel absorbent layers 34 and 35. The openable end formed by the separation of the topsheet and the backsheet allows the removal and replacement of the removable absorbent core components and may be resealable to provide a substantial degree of liquid impermeability when closed. The openable end may be made resealable, for example, with a suitable releasable and resealable adhesive 56 known in the art.

As can be seen in FIG. 13 and in FIG. 16, the openable chassis pocket 5 generally has an outer end 27 and an inner end 28 corresponding to the outer end 31 and the inner end 32, respectively, of the back panel 30. In the exemplary embodiments shown in FIG. 13 and FIG. 16, the outer end 27 of the openable chassis pocket coincides with its openable end 41. The inner end of the openable chassis pocket may be formed in several ways. For example, as shown in FIG. 13, the inner end may be formed at the area of attachment of the backsheet pocket sheet 45 to the backsheet. As described above, the backsheet, the topsheet, and the non-removable absorbent core component may be secured, attached, or affixed to each other in a variety of configurations. Thus, as another example of the formation of the inner end of the openable chassis pocket, an area of attachment of the non-removable absorbent core component to the chassis, e.g., to the backsheet, the topsheet, or both, in the crotch region may form the inner end of the openable chassis pocket.

Figure 17:
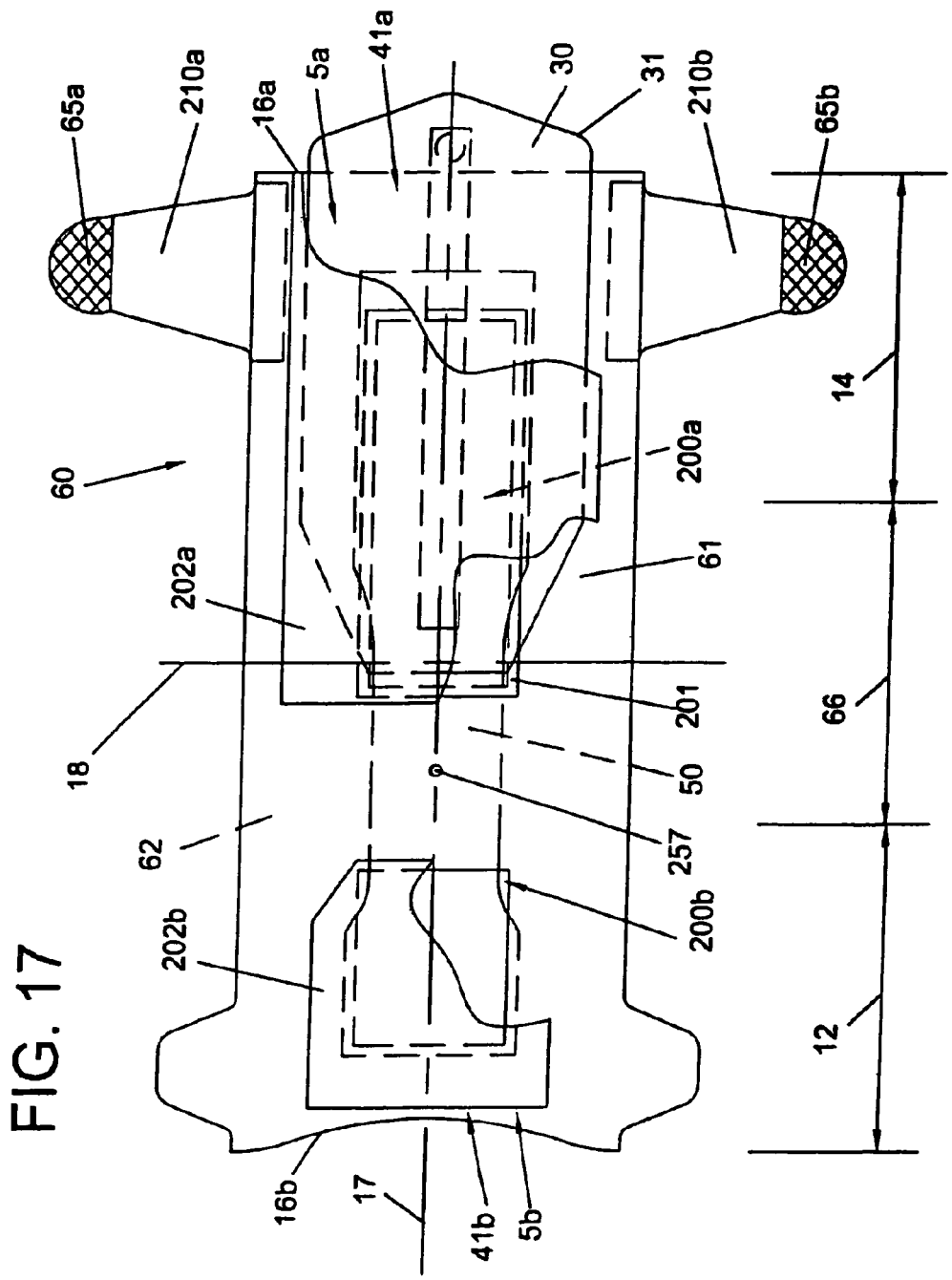
FIG. 17 is a plan view of another exemplary diaper in its flat-out, uncontracted state, i.e., with all elastic induced contraction pulled out, with portions of the structure being cut away to more clearly show the construction of the diaper, and with the portion of the diaper that contacts the wearer facing the viewer, showing an apertured topsheet.
Figure 18:
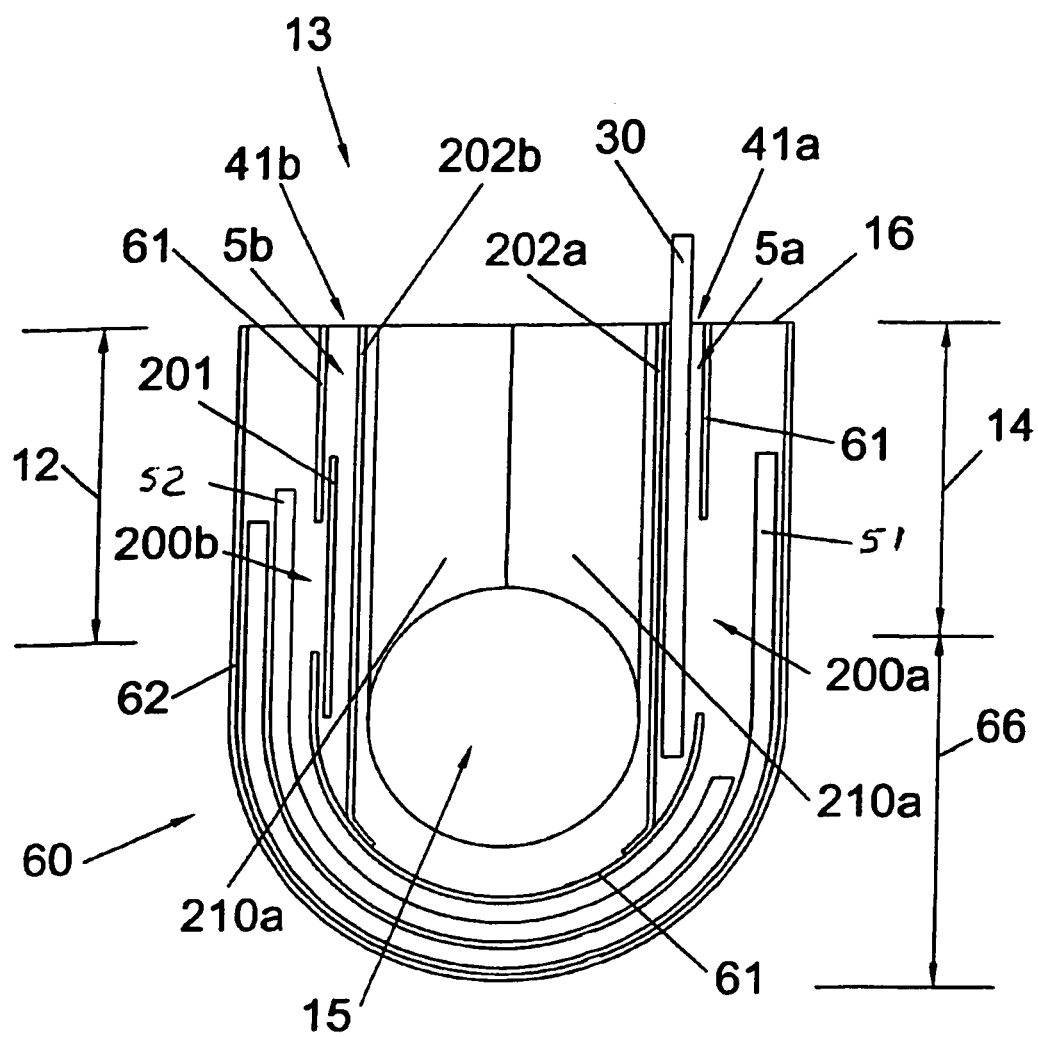
FIG. 18 is a cross-section view of an exemplary pants-type diaper having an apertured topsheet.

In alternative embodiments, as shown in FIG. 17 and FIG. 18, a topsheet pocket sheet 202 may be affixed on the wearer-facing surface of the topsheet 61 to form an openable chassis pocket 5 between the topsheet pocket sheet and the topsheet. The openable chassis pocket 5 formed by the topsheet pocket sheet 202 may have its openable end 41 adjacent to the nearest waist end edge 16. The openable chassis pocket may be reclosable and may be resealable, and may be positioned so that an inserted back panel is urged into capillary liquid communication with the center section. The topsheet pocket sheet may be resilient, pliable, and liquid pervious and may be formed of the same material as the topsheet.

As is also shown in FIG. 17 and in FIG. 18, in some exemplary embodiments having such an openable chassis pocket 5 formed by a topsheet pocket sheet 202, the topsheet 61 may have a topsheet aperture 200 allowing face-to-face contact and capillary liquid communication between a replaceable absorbent core component disposed in the openable chassis pocket, such as the back panel 30, and a non-removable absorbent core component, such as the center section 50, disposed adjacent to an opposing surface of the topsheet. Such a topsheet aperture may have an area of approximately 1 $cm^2$ or greater, and a smaller of its length and width dimensions may be approximately 5 mm or greater. Such a topsheet aperture may have a generally rectangular shape, a generally circular shape, or any other geometric shape having a ratio of smallest dimension to greatest dimension of from 1:1 to approximately 1:100, including all intermediate ratios. In some exemplary embodiments, such a topsheet aperture may be covered with a layer of a permanently hydrophilic fibrous material. This topsheet aperture covering layer 201 may be formed of fibers that are naturally hydrophilic or of fibers that have been treated to make them permanently hydrophilic in the sheet structure. Alternatively, the topsheet aperture may be covered with a mesh having openings sufficiently large to allow the direct face-to-face contact of the absorbent layers disposed on either side of the topsheet. Suitable non-limiting examples of materials that can be used to cover the topsheet aperture include a permanently hydrophilic non-woven available from SciMAT Limited of Swindon, U.K. under product code 900/20, a mesh material such as a 100% nylon netting available from WYLA, Inc. of New York, N.Y., U.S.A. under product designation RT80, and a tissue such as a cellulose tissue available from Georgia-Pacific Corporation of Atlanta, Ga., U.S.A. under the designation of 65588. Another suitable material for use as the topsheet aperture covering layer comprises a bonded structure of curly cellulosic fibers, which may also include high surface area fibers as described herein.

As described in the chassis description, an elastic waistband 67 may be disposed in the waistband region 63 between the waist end edge 16 and the adjacent end of the absorbent core, as shown in FIG. 1 and in FIG. 2. When such an elastic waistband is disposed adjacent to an opening formed by the separation of the topsheet and the backsheet along a waist end edge, the waistband may serve to make the opening elastically openable and self-closing. For example, such an elastic waistband, formed as either a separate element affixed to the backsheet or as an extension of the backsheet in the waistband region, may exert a contractive force tending to draw the waist end edge of the backsheet at the periphery toward the topsheet, thus tending to close the openable end of the openable chassis pocket when it is released.

As another example, an elastic waistband, formed as either a separate element affixed to the topsheet or as an extension of the topsheet in the waistband region, may exert a contractive force tending to hold the waist end edge of the topsheet against the body of the wearer at all times, including when the waist end edge of the backsheet is pulled away from the topsheet to form the opening and thereby gain access into the openable chassis pocket. In addition, as described above in the chassis description, a flexible substrate forming the chassis, such as the backsheet and the topsheet, may be elasticized or otherwise extensible. Thus, the superposed or layered portions of both the topsheet and the backsheet in the openable area along the waist end edge may be elastically contractible, either by means of a waistband or otherwise. In such an embodiment, when the backsheet is pulled away for access into the openable chassis pocket, the waist end edge of the topsheet may be held elastically against the body of the wearer, thereby facilitating the access, and the opening may also be self-closing by means of the elastic contraction of the waist end edge of the backsheet when it is released.

In yet another example, a first extensible waistband may be sandwiched between and attached to the wearer-facing layer and the garment-facing layer and a second extensible waistband attached to or forming an extension of only the garment-facing layer may be disposed adjacent to the first extensible waistband in a position farther from the adjacent waist end edge, i.e., toward the crotch region, relative to the first extensible waistband. The garment-facing layer, e.g., the backsheet, in such an embodiment may include an aperture between the two extensible waistbands providing access into the openable chassis pocket formed between the wearer-facing layer and the garment-facing layer when the second extensible waistband is separated from the first extensible waistband. In one scenario, at least the second extensible waistband is elastically extensible. In some embodiments, the portion of the garment-facing layer surrounding the second extensible waistband may also be extensible.

In still another example, an extensible waistband may include a first portion sandwiched between and attached to the wearer-facing layer and the garment-facing layer in a portion of the waistband region adjacent to the waist end edge and a second portion attached to only the garment-facing layer and disposed farther from the adjacent waist end edge, i.e., toward the crotch region, relative to the first portion of the extensible waistband. The extensible waistband and the garment-facing layer, e.g., the backsheet, in such an embodiment may each include an aperture between the two portions of the extensible waistband providing access into the openable chassis pocket formed between the wearer-facing layer and the garment-facing layer when the second portion is separated from the first portion. The extensible waistband may be elastically extensible. In some embodiments, the portion of the garment-facing layer surrounding the extensible waistband may also be extensible.

In a further example, a first extensible waistband may be attached to the wearer-facing layer and a second extensible waistband attached to or forming an extension of the garment-facing layer may be disposed adjacent to the first extensible waistband in a position closer to the adjacent waist end edge, i.e., farther from the crotch region, relative to the first extensible waistband. The wearer-facing layer and the garment-facing layer may be separable in the waistband region, providing access into the openable chassis pocket formed between the wearer-facing layer and the garment-facing layer when the second extensible waistband and the garment-facing layer of the chassis are separated from the first extensible waistband and the wearer-facing layer of the chassis. In some embodiments, at least the second extensible waistband is elastically extensible. In some embodiments, the portion of the garment-facing layer surrounding the second extensible waistband may also be extensible.

Figure 19:
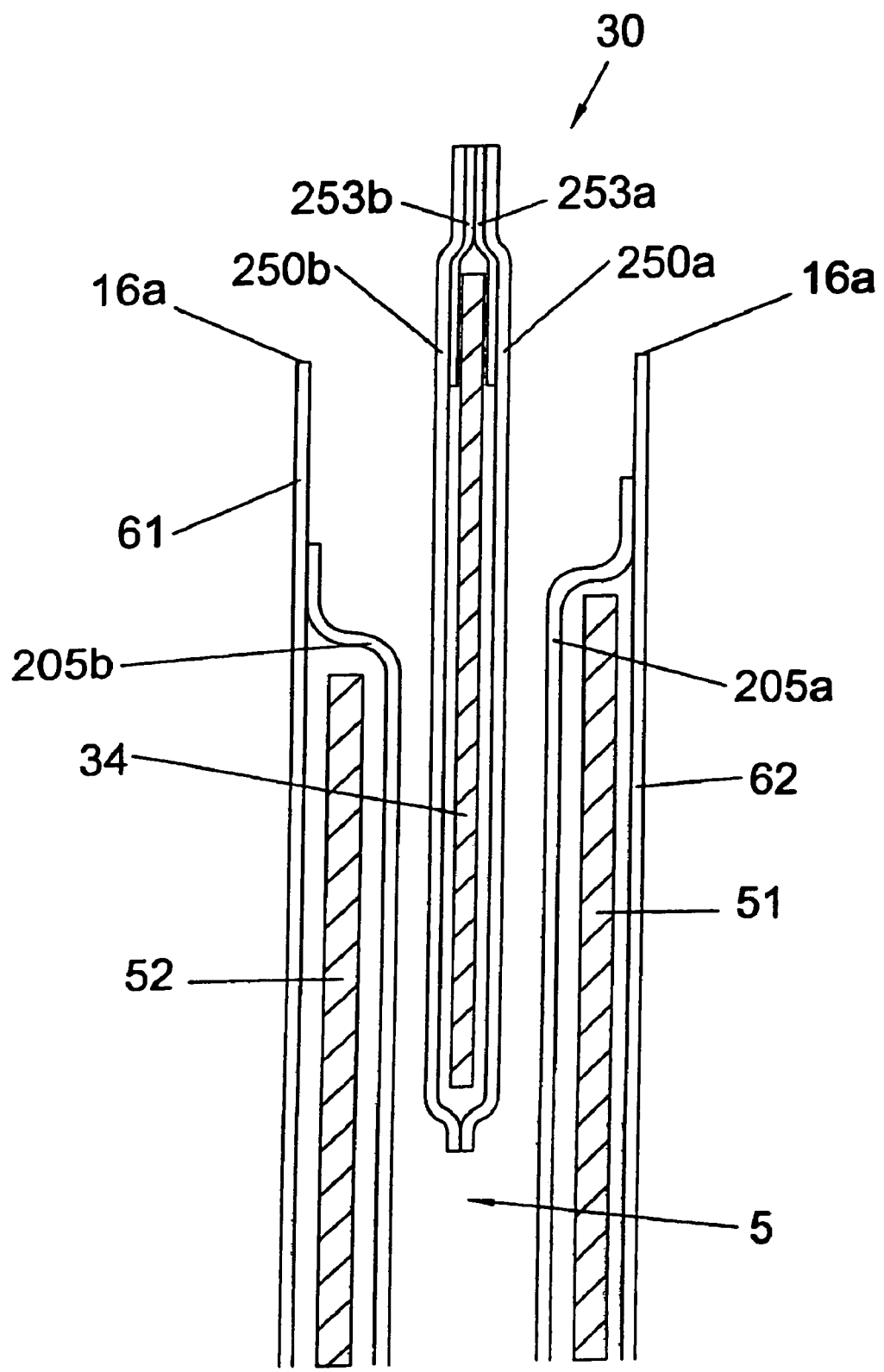
FIG. 19 is a partial section view showing chassis layers and non-removable absorbent core layers in relation to a replaceable absorbent core component.

As shown in FIG. 19, a portion of the non-removable core component, such as the uppermost absorbent layer 52 of the center section, may be disposed between a liquid pervious wearer-facing layer of the chassis, such as the topsheet 61, and another liquid pervious layer 205 of the chassis. One or both of the liquid pervious layers may form a portion of the openable chassis pocket 5 adapted to receive the replaceable absorbent core component, e.g., back panel 30. An acquisition member, a distribution member, or an acquisition/distribution member of the non-removable core component may be disposed between the liquid pervious layers. In some embodiments, at least one of the liquid pervious layers may be disposed between two members of the non-removable core component.

Alternatively, a portion of the non-removable core component, such as the lowermost absorbent layer 51 of the center section shown in FIG. 19, may be disposed between a liquid pervious layer 205 of the chassis and a liquid impervious layer of the chassis, such as the backsheet 62. One or both of the liquid pervious layer and the liquid impervious layer may form a portion of the openable chassis pocket 5 adapted to receive the replaceable absorbent core component, e.g., back panel 30. A distribution or acquisition/distribution member of the non-removable core component may be disposed between the liquid pervious and the liquid impervious layers. In some embodiments, the liquid pervious layer may be disposed between two members of the non-removable core component.

In order to provide additional space within the openable chassis pocket, the surfaces forming the openable chassis pocket, e.g., the topsheet, the backsheet, the barrier leg cuffs, etc., may be formed from extensible materials, or elastically extensible materials, to permit the expansion of the pocket. These materials may be extensible in at least in the lateral direction or in both the lateral and longitudinal directions. This expansibility of the openable chassis pocket may facilitate the removal and/or the insertion of a replaceable core component and may also be useful in embodiments in which the replaceable core component includes an absorbent layer that expands as it absorbs liquid.

In some exemplary embodiments, the openable chassis pocket and the replaceable core component may be "keyed" to each other, so as to prevent the insertion of the replaceable core component in any orientation other than a predetermined orientation contemplated in the design of the replaceable core component. Thus, the openable chassis pocket may be shaped and the replaceable core component may be correspondingly shaped to fit within the shaped openable chassis pocket.

Figure 20:
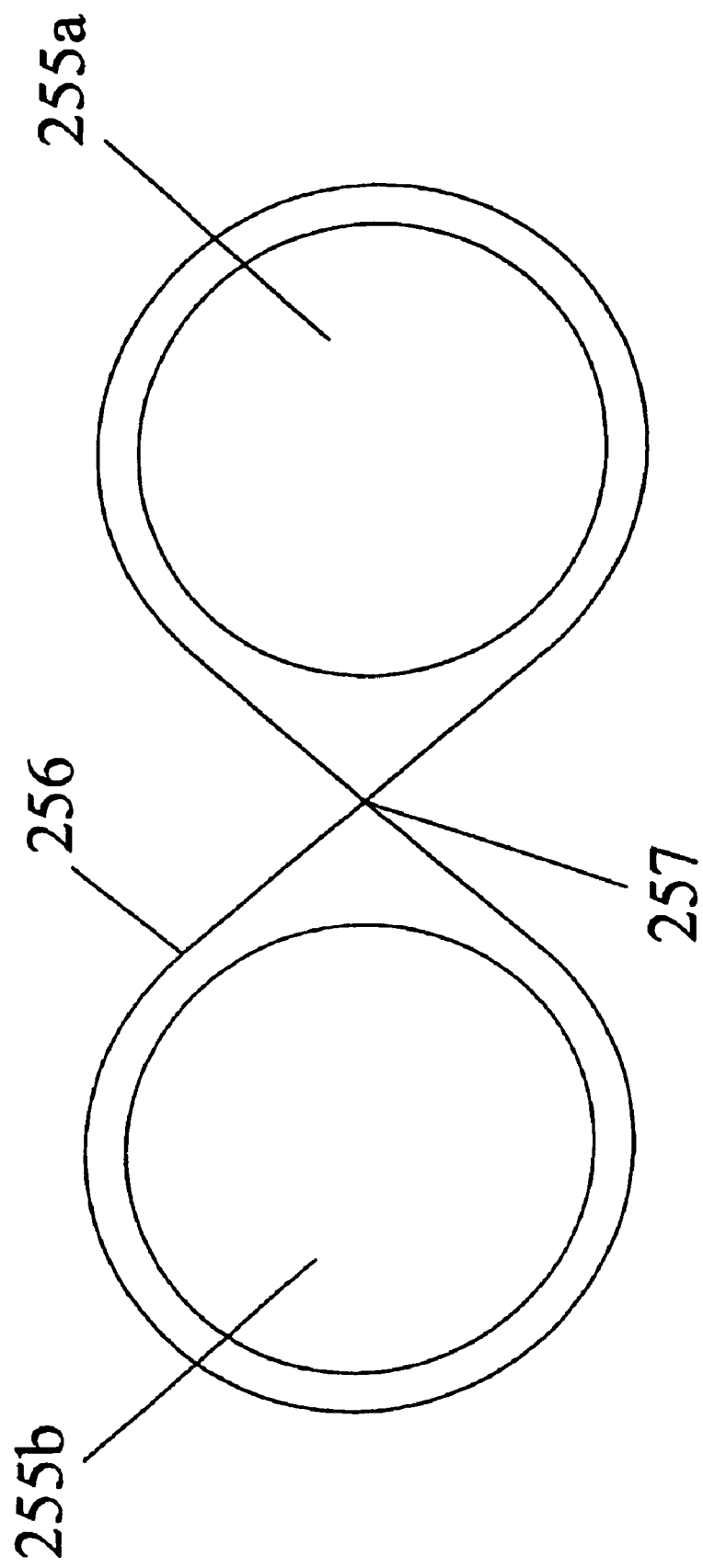
FIG. 20 is simplified plan view illustrating the method of determining the crotch point of an absorbent article.

In some embodiments, the openable chassis pocket may extend from a waist region into the crotch region as far as the crotch point. In particular, the openable chassis pocket may extend from the respective waist region into the crotch region no farther than the crotch point of the absorbent article, so as to thereby limit the depth of insertion of a replaceable core component to no farther than the crotch point. The "crotch point" of an absorbent article and of the absorbent article's absorbent core is determined by placing the article on a wearer of the physical size for which the absorbent article is designed and who is in a fully upright standing position with his or her feet a shoulder width apart and then placing an extensible filament 256 around the legs 255 in a figure eight configuration as shown in FIG. 20. The point in the absorbent article and the absorbent core corresponding to the point of intersection 257 of the filament is considered to be the crotch point of the absorbent article and of the absorbent core. It is understood that the crotch point is determined by placing an absorbent article in the intended manner on a standing wearer of the correct size for the article and determining where the crossed filament would contact the absorbent article and/or the absorbent core.

The Replaceable Absorbent Core Component

At least a portion of one major surface of the replaceable core component may be pervious to liquid for the absorbent layer of the replaceable core component to be in capillary liquid communication with the non-removable core component. This pervious portion of the major surface may be described as forming a permeable liquid transfer region. In exemplary embodiments, at least about 20% of the area of this major surface is liquid pervious. In some embodiments, at least about 50% or at least about 80%, of this major surface may be liquid pervious. The permeable liquid transfer region may be covered by a liquid pervious sheet. Also, the replaceable core component may have permeable liquid transfer regions in both of its major surfaces. In one example, the back panel 30 has the permeable liquid transfer region in its upper major surface formed by the upper packet layer and the permeable liquid transfer region in its lower major surface formed by the lower packet layer.

Except for the permeable liquid transfer region or regions, the major surfaces of the replaceable core component may be liquid impervious. In particular, it may be desirable for the outer end segment or at least the area of the pull tab at the outer end to be liquid impervious in order to prevent the escape or the leakage of liquid from this portion of the replaceable core component. The prevention of leakage from this area may enable a caregiver to avoid contact during the removal of a used replaceable core component with the liquid contained in it. A liquid impervious region may be formed by a liquid impervious layer disposed between the absorbent layer of the replaceable core component and the layer forming the surface, such as by the liquid impervious layer 253 disposed between the absorbent layer 34 of the back panel 30 and the packet layer 250 shown in FIG. 19. Alternatively, the liquid impervious region may be formed by a liquid impervious layer forming the major surface or by the treatment of an otherwise liquid pervious layer to render it liquid impervious in the desired region. For example, portions of the packet layers between the permeable liquid transfer regions and the outer end of the back panel may either include a liquid impervious sheet material or be treated to become liquid impervious.

Figure 21:
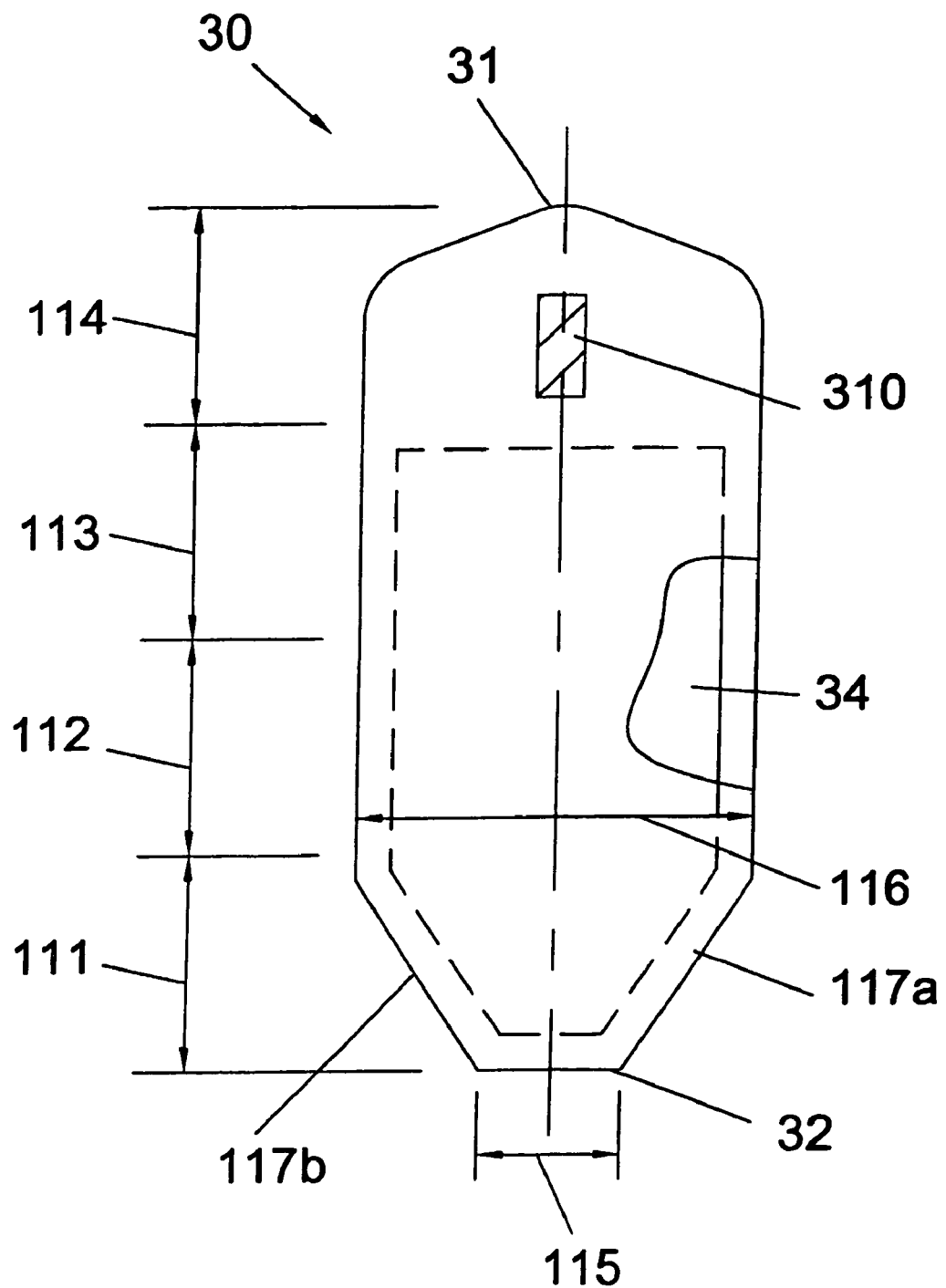
FIG. 21 is a plan view showing a replaceable absorbent core component illustratively divided into four longitudinal segments.

The replaceable core component, e.g., the back panel 30 shown in FIG. 21, has an inner end 32 and an outer end 31 and may be divided longitudinally for descriptive purposes into successive first, second, third, and fourth segments defined by respective quarters of its length. The replaceable core component may have two major surfaces having substantially equal areas and, for descriptive purposes, the area of each of the four longitudinal segments may be expressed as the area of the portion of one of the major surfaces falling within the segment. When so divided, the first segment 111, which is also referred to herein as the inner end segment, includes the inner end and may have an area less than an area of any one of the second, third, and fourth segments. For example, the inner end of the replaceable core component may have a smaller width 115 than the width 116 of the second segment 112 and may have converging sides 117, i.e., the inner end segment may convergingly taper toward the inner end. The fourth segment 114, which is also referred to herein as the outer end segment, includes the outer end and may have an area less than the area of at least one of the second segment or the third segment 113. The areas of the second and third segments may be substantially equal or the second segment may have an area less than that of the third segment. In some embodiments, the four segments may have the following areas. The first segment may have an area of between 10 cm$^2$ and 110 cm$^2$ or between 30 cm$^2$ and 70 cm$^2$. The second segment may have an area of between 10 cm$^2$ and 110 cm$^2$ or between 30 cm$^2$ and 100 cm$^2$. The fourth segment may have an area of between 10 cm$^2$ and 110 cm$^2$ or between 30 cm$^2$ and 100 cm$^2$. The third segment may have an area of between 10 cm$^2$ and 110 cm$^2$ or between 30 cm$^2$ and 100 cm$^2$. Based on these areas, the overall surface area of the replaceable core component may be between 40 cm$^2$ and 440 cm$^2$ or between 120 cm$^2$ and 370 cm$^2$.

Similarly, the absorbent structure of the replaceable core component, e.g., an absorbent layer 34 of back panel 30, has an inner end 238 and an outer end 239 and may be divided longitudinally for descriptive purposes into four successive segments from its inner end to its outer end, corresponding to the four segments of the replaceable core component as a whole. Like the replaceable core component, the absorbent structure may have two major surfaces having substantially equal areas and, for descriptive purposes, the area of each of the four longitudinal segments of the absorbent structure may be expressed as the area of the portion of one of the major surfaces falling within the segment. In some embodiments, an absorbent layer may extend from the first segment 111 of the replaceable core component to the fourth segment 114 of the replaceable core component, as in FIG. 22. In other embodiments, the absorbent layer may extend only from the first segment 111 to the second segment 112 or to the third segment 113 of the replaceable core component, as in FIG. 23. The first absorbent layer segment, or inner end segment of the absorbent layer, includes the inner end of the absorbent layer and may have an area less than an area of any one of the other segments of the absorbent layer. For example, the inner end of the absorbent layer may have a width smaller than a maximum width of the second segment of the absorbent layer and may have converging sides, i.e., the inner end segment may convergingly taper toward the inner end. The absorbent layer may have an overall shape similar to the shape of the replaceable core component, as a whole. For example, the absorbent layer may have a shape identical to that of the replaceable core component, but reduced in scale, so as to fit at some distance inside the perimeter of the replaceable core component. Alternatively, the absorbent layer and overall replaceable core component may have different shapes. For example, the overall replaceable core component may have a substantially rectangular shape, while the absorbent layer inside it may have a tapered shape.

It is to be appreciated that the replaceable core component can be configured in various ways and provided with various features, as discussed below. Such features may relate to the positioning and disposal of a replaceable core component.

For example, the replaceable core component may include a pull tab that can be used to remove the core component from the chassis. In another scenario, the replaceable core component may include an extensible covering layer attached to one end segment of the replaceable core component. The extensible covering may be adapted to cover the replaceable core component once fully withdrawn from the chassis. As such, the extensible covering may prevent contact with a soiled portion of the replaceable core component during disposal.

In another example, the replaceable core component may include a location stabilizer 310, such as shown in FIG. 21, adapted to releasably retain the replaceable core component in its fully inserted position, such as by releasably attaching the replaceable core component to the chassis in the waist region, in the crotch region, or in both regions. The location stabilizer may include a mechanical surface fastener such as either a hook or a loop member disposed on the replaceable core component and adapted to engage a complementary member disposed on the chassis, or to engage a non-woven surface of the chassis. In some embodiments, the location stabilizer may include an adhesive disposed on the surface of the replaceable core component and adapted to releasably engage a surface of the chassis. Alternatively, the chassis may include a location stabilizer adapted to releasably engage a surface of the replaceable core component. In some embodiments, the location stabilizer may include a tab adapted to be inserted into a slot and thereby releasably retain the replaceable core component in its fully inserted position. For example, a tab on the replaceable core component may be insertable into a slot in the chassis or vice versa. Such a tab disposed at the outer end segment of the replaceable core component may be inserted into a corresponding slot to serve as the location stabilizer while the replaceable core component is fully inserted and then may be removed from the slot and used as the removal pull tab when the replaceable core component is removed from the chassis.

Some embodiments of the replaceable core component may include an insertion depth indicator to provide an indication when a predetermined position of the replaceable core component relative to the chassis is reached. In one example, the insertion depth indicator may include a mechanical insertion depth indicator providing tactile feedback. In some exemplary embodiments, an outer surface of the replaceable core component or an element disposed on the outer surface may have a directional coefficient of friction relative to the adjacent surfaces of the chassis and thereby provide tactile feedback related to whether or not the replaceable core component is being inserted in the intended end-to-end orientation.

In some exemplary embodiments, opposing outer surfaces of the replaceable core component may have different coefficients of friction relative to the adjacent surfaces of the chassis and thereby provide tactile feedback related to whether or not the replaceable core component is being inserted in the intended orientation of its predetermined wearer-facing and garment-facing surfaces. The elements having the directional frictional characteristics described above may be combined in various ways to provide tactile feedback related to both related to whether or not the replaceable core component is being inserted in the intended end-to-end orientation and whether or not the replaceable core component is being inserted in the intended orientation of its predetermined wearer-facing and garment-facing surfaces.

In some embodiments, the replaceable core component may include an openable insertion pocket 260 into which a finger or fingers or an insertion tool 270 may be inserted for the application of a force to insert the replaceable core component into the chassis in the intended predetermined orientation. As shown in FIG. 24 and FIG. 25, such an insertion force may be applied in a direction indicated by the arrow 320 from the outer end toward the inner end of the replaceable core component, e.g., in a direction from the outer end 31 toward the inner end 32 of the back panel 30. For example, the back panel 30 may have a piece of sheet material 261 joined to its outer surface by continuous linear bonds or by an array of spot bonds, or any combination thereof, to form the openable insertion pocket having an outer end edge 265, an inner end 264, and an openable end 263 located at its outer end edge and facing toward the outer end 31 of the back panel 30. The openable insertion pocket may be of sufficient size to accept only a finger or fingers, of sufficient size to accept an entire hand of a caregiver, or of sufficient size to accept an insertion tool. The openable insertion pocket may also be formed internally to the replaceable core component. In addition, the internal insertion pocket may include an inverting pull tab disposed inside the internal insertion pocket. When the inverting pull tab is pulled toward the outer end of the replaceable core component, the replaceable core component is inverted, i.e., turned inside out, such that the original outer layers of the replaceable core component are drawn inside and the original inner layers of the internal insertion pocket are drawn to the outside of the inverted replaceable core component.

In some embodiments, the replaceable core component extends only from the crotch region to one of the waist regions of the article. However, the replaceable core component may extend from the crotch region beyond a waist end edge of one of the waist regions, so that the outer end of the replaceable core component is exposed and thereby visible when the absorbent article is worn. A portion of the replaceable core component extending beyond the waist end edge may include a liquid presence indicator adapted to provide an indication of a wetted condition of the replaceable core component. The liquid presence indicator may include multiple strips of wicking material, which may have differing characteristics such as the lengths of the strips, the thicknesses of the strips, the shapes and areas of the strips, the pore sizes of the wicking materials used in the various strips, the absorbent capacities of the strips, the degrees of hydrophilicity of the strips, and etc. A single wicking strip may also be used.

In some exemplary embodiments, the liquid presence indicator may include an indicating composition disposed on an absorbent layer of the replaceable core component, such as a storage member or a storage/redistribution member. Such an indicating composition may be disposed on the absorbent layer in the outer end segment of the replaceable core component. The indicating composition may provide a visible indication and may include a pH-activated or moisture-activated material, which may be applied to the absorbent layer in the form of a hotmelt adhesive or a water-soluble dye in some exemplary embodiments. The visible liquid presence indication means may be disposed above the waist end edge of the chassis when the replaceable core component is inserted to the intended predetermined depth in the chassis.

However, in some embodiments, the visible indication means may be disposed below the waist end edge, i.e., between the backsheet and the wearer in the waist region of the article, when the replaceable core component is inserted to the intended predetermined depth.

Some exemplary embodiments may have a "dipstick" type visible liquid presence indicator, in which an absorbent strip can be moved through a slit in an outer layer of the replaceable core component between a fully inserted position within the replaceable core component and a partially inserted position, thereby exposing an inner portion of the visible liquid presence indication absorbent strip and facilitating a determination of the level to which the replaceable core component has been wetted. The usage of such a "dipstick" type visible liquid presence indication absorbent strip is similar to that of using a dipstick to check the fluid levels in an automobile engine, the fuel level in an aircraft fuel tank, or the level in an in-ground storage tank. The "dipstick" type visible liquid presence indication absorbent strip can include a litmus paper-like substrate that changes color in a wetted area, or can include a series of visible liquid presence indication means, each of which undergoes a visible change in response to a liquid presence or to the pH of a liquid contacting the indication means. The dipstick approach enables the user to assess the actual level of liquid loading in the replaceable core component, in addition to determining the presence of liquid.

In some embodiments, the liquid presence indicator may include a water-sensitive restraining element whose dimension, tensile strength, resistance to compression, resistance to bending, or resistance to buckling is altered when it is contacted by water. The water-sensitive restraining element may include a water soluble material or a material that weakens, but does not dissolve, when wetted, such as cellulosic material.

In some embodiments, a liquid presence indicator having a similar structure may provide a tactile indication of the presence of liquid in the replaceable core component. For example, when released, the elastic element may move a movable tactile indicator strip to a predetermined position in which the thickness of the strip provides the tactile impression of a raised area or a protuberance. As another example, when released, the elastic element may move a movable tactile indicator strip away from its initial position in which the thickness of the strip provided the tactile impression of a raised area or a protuberance and thereby eliminate that tactile impression, i.e., make the initially raised or protruding area feel smooth or flat.

The Insertion Tool

In some embodiments, the replaceable core component may be constructed with materials providing enough stiffness that allows the replaceable core component to be inserted into the chassis without buckling. To provide additional comfort during wear, the replaceable core component may be relatively soft, relatively thin, and relatively flexible. However, the flexibility may make the insertion of the replaceable core component, by itself, difficult. For example, an attempt to insert the replaceable core component by grasping its outer end and pushing it into the chassis may result in the replaceable core component collapsing or buckling due to the sliding resistance between its outer surfaces and the adjacent surfaces of the chassis. Similarly, an attempt to insert the replaceable core component by grasping its inner end and inserting the grasping hand into the chassis may lead to wrinkling or folding of the replaceable core component. Also, the grasping hand may be too large to fit into the space into which the replaceable core component is being inserted and, therefore, only a partial insertion may be achieved.

Thus, the use of an insertion tool having a suitable thickness, a suitable stiffness, and a suitable buckling resistance may facilitate the insertion of the replaceable core component. Therefore, an absorbent article may include an insertion tool for use in the application of a force to insert the replaceable core component into the chassis in the intended predetermined orientation. The use of such an insertion tool may obviate the need for a caregiver to insert her hand into the absorbent article when inserting a replaceable core component. Also, a suitable insertion tool may be significantly thinner than a human hand and thus facilitate the deeper insertion of the replaceable core component into the chassis, including when the chassis, or the margin of the openable end of an openable chassis pocket, is limited in its extensibility to accommodate the insertion. In different embodiments, the insertion tool may be withdrawn following the insertion of the replaceable core component or may remain in the chassis. Also, the insertion tool may be used without being attached to the replaceable core component, may be attached to the replaceable core component for its insertion and then detached from the replaceable core component, or may remain attached to the replaceable core component.

The insertion tool 270 may be inserted into an insertion pocket 260 attached on the outside of a replaceable core component, such as in the exemplary embodiment shown in FIG. 24 and FIG. 25, or it may be inserted into an internal insertion pocket formed internally of the replaceable core component, as described elsewhere in this disclosure. In some embodiments, two insertion tools may be inserted into two insertion pockets disposed on the opposing major surfaces of the replaceable core component. When used in this manner, the two insertion tools may act as barriers preventing the exposure of the replaceable core component, for example, to the hand of a caregiver inserting the replaceable core component into the absorbent article. In addition, the surfaces of the two insertion tools may have a relatively low coefficient of friction to the adjacent materials of the chassis and thereby facilitate the insertion of the replaceable core component. Once it is inserted into the insertion pocket 260, the insertion tool 270 may be used to exert an insertion force in the direction indicated by the arrow 320 to insert the replaceable core component into the chassis. Then, the insertion tool may be withdrawn from the chassis in the opposing direction indicated by the arrow 321.

Alternatively, the insertion tool may be releasably attached to the replaceable core component in a manner that is suitable for the effective insertion of the replaceable core component into the chassis. In such an embodiment, after the replaceable core component is inserted, the insertion tool may be released from the replaceable core component as the insertion tool is withdrawn from the chassis.

Rather than being joined or attached to the replaceable core component either directly or through an intermediate member, the insertion tool may have one or more protuberances, such as angled teeth or hooks, that engage the layer forming the outer surface of the replaceable core component when the insertion tool is slid along the outer surface in a first direction, and that disengage or fail to engage when the insertion tool is slid along the outer surface in an opposing second direction. Alternatively, the insertion tool may engage such protuberances on the outer surface of the replaceable core component. In either configuration, the movement of the insertion tool in the first direction applies an insertion force to the replaceable core component, while the movement of the insertion tool in the second direction disengages the insertion tool from the replaceable core component, thus leaving the replaceable core component in the inserted position. A surface of the insertion tool having a directional coefficient of friction relative to the outer surface layer of the replaceable core component may perform the same function as the protuberance by providing greater resistance when slid along the outer surface of the replaceable core component in the insertion direction and lesser resistance when withdrawn in the opposing direction.

The insertion tool may include an insertion depth indicator to provide an indication when a predetermined position of the insertion tool corresponding to a predetermined position of the replaceable core component relative to the chassis is reached. In general, the insertion tool may include any of the forms of an insertion depth indicator described with regard to the replaceable core component. For example, the insertion depth indicator may include a visible indicator such as a line positioned adjacent to the outer end of the insertion tool such that the line is aligned with the waist end edge of the chassis when the predetermined position is reached. In another example of a visible insertion depth indicator, a graphical object on the insertion tool may align with an adjacent graphical object on the chassis to form a composite graphical object when the predetermined position is reached, similarly to the way in which a similar graphical object on the replaceable core component is herein described as aligning.

In some exemplary embodiments, the insertion tool's insertion depth indicator may include a mechanical indicator providing tactile feedback. For example, an outer surface of the insertion tool may have a directional coefficient of friction relative to the adjacent surfaces of the chassis and thereby provide tactile feedback related to whether or not the insertion tool and the replaceable core component are being inserted in the intended end-to-end orientation. In another example, opposing outer surfaces of the insertion tool may have different coefficients of friction relative to the adjacent surfaces of the chassis and thereby provide tactile feedback related to whether or not the insertion tool and the replaceable core component are being inserted in the intended orientation of the replaceable core component's predetermined wearer-facing and garment-facing surfaces.

Figure 26:
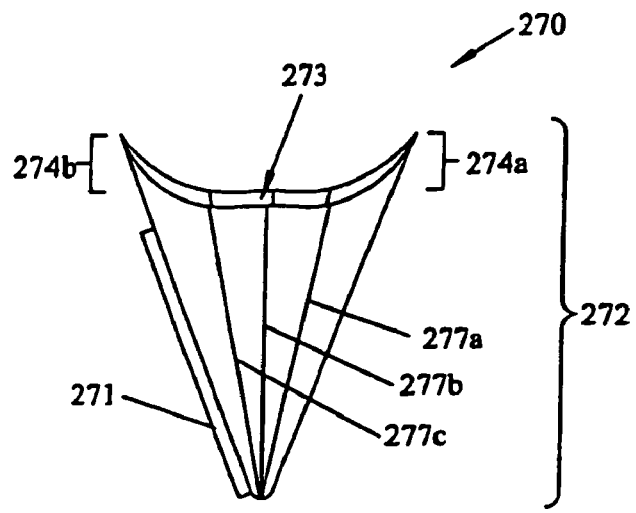
FIG. 26 is a side elevation view showing an insertion tool formed by a card-like element attached to a bag-like element.
Figure 27:
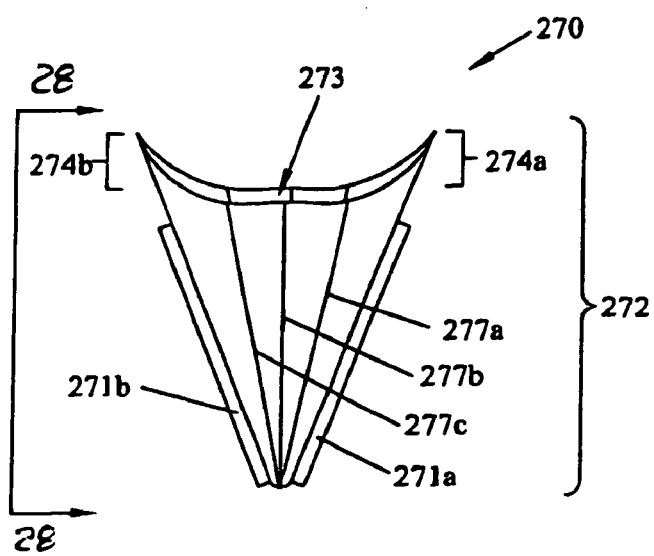
FIG. 27 is a side elevation view showing an insertion tool formed by two card-like elements attached to a bag-like element.
Figure 28:
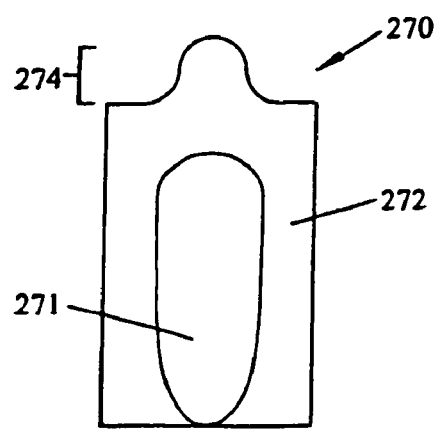
FIG. 28 is an elevation view showing one major surface of the insertion tool of FIG. 27.

The insertion tool may include a planar card-like element 271, as shown in FIG. 26. Such an insertion tool may also include a bag-like element 272 forming an openable insertion tool pocket 273, as shown in an open state in FIG. 26. The bag like element may be joined to one side of the planar card-like element, as in FIG. 26, or alternatively, the bag-like element may be disposed between and joined to two planar card-like elements, as shown in FIG. 27. The bag-like element may be made of an extensible sheet material or may be formed of a sheet having folds or pleats 277 so as to be expandable for opening. The openable insertion tool pocket 273 may be of sufficient size to accept and retain a replaceable core component. Thus, the openable insertion tool pocket may be used to contain an unused replaceable core component prior to use or to accept and contain a used replaceable core component for disposal. The bag-like structure of the insertion tool may include a closure means, such as a tie-style closure that may include one or more closure tabs 274, as shown in FIG. 28, a drawstring closure, a mechanical fastener, a zipper, a button, a snap, an adhesive closure, or another closure means known in the art. In embodiments in which the unused replaceable core component is disposed inside the openable insertion tool pocket, this closure means may be used to secure the replaceable core component inside the pocket prior to its insertion into the absorbent article. This closure means may also be used to secure a used replaceable core component inside the openable insertion tool pocket after its removal from the absorbent article.

In yet another embodiment, the insertion tool may have a substantially planar portion having a generally uniform thickness and a portion adjacent to its inner end having a greater thickness and thereby serving as a "plow" to separate the separable layers of the chassis as the insertion tool in inserted into the absorbent article.

In embodiments in which the openable chassis pocket and the replaceable core component are "keyed" to each other, so as to prevent the insertion of the replaceable core component in any orientation other than a predetermined orientation contemplated in the design of the replaceable core component, the insertion tool may be correspondingly keyed to the openable chassis pocket and the replaceable core component. Thus, the openable chassis pocket may be shaped and the insertion tool may be correspondingly shaped to fit within the shaped openable chassis pocket.

Methods of Use as a Swim Pant

As previously mentioned, the present disclosure provides for the use of absorbent articles, such as those described above, as a swim pant. Those skilled in the art will recognize that additional exemplary embodiments of absorbent articles providing access to a removable and replaceable absorbent core component or absorbent insert are possible. Furthermore, it is contemplated that additional combinations of the absorbent core components, the absorbent core members, the placement of the absorbent core components and members, and the absorptive characteristics may be used, with the desired functional requirements influencing the ultimate design. Specifically, not only the illustrated embodiments, but all structurally feasible combinations of the disclosed elements and configurations are contemplated. It is to be appreciated that such additional exemplary embodiments of absorbent articles and core components may be used as a swim pant according to the disclosed methods.

As discussed in more detail below, the present disclosure provides methods for using and wearing absorbent articles as a swim pant when the replaceable core component is removed. For the purposes of the methods described below, an absorbent article in accordance with above disclosure can be selectively configured as a higher absorbency diaper (i.e. higher absorbency configuration) and a swim diaper (i.e. swim configuration). More particularly, the absorbent article may be selectively placed in the higher absorbency configuration by placing a replaceable core component in capillary liquid communication with a low absorbency core component. As mentioned above, the low absorbency core component can be configured as a non-removable core component. For example with reference to FIG. 5, the absorbent article may be selectively placed in the higher absorbency configuration by inserting the replaceable core component or back panel 30 into the openable chassis pocket 5, thereby placing the replaceable core component in capillary liquid communication with a non-removable core component or center section 50. Alternatively, the absorbent article may be selectively placed in the swim configuration by removing the replaceable core component from capillary liquid communication with the low absorbency, non-removable, core component. For example with reference to FIG. 5, the absorbent article may be selectively placed in the swim configuration by removing the replaceable core component or back panel 30 from the openable chassis pocket 5, thereby removing the replaceable core component from capillary liquid communication with the non-removable core component or center section 50. It should be appreciated that low absorbency core components and the replaceable core components can be configured with different absorbent materials and/or different quantities of such materials. For example, in some embodiments of absorbent articles that utilize absorbent gelling materials (AGM), the replaceable core component may contain AGM while the low absorbency core contains no AGM.

In one method of use as a swim pant, an absorbent article can be selectively configured as a high absorbency diaper when not engaging in water-related activities and then converted into a swim diaper shortly before engaging in water-related activities without having to remove the diaper from the wearer. In one example, an absorbent article having a low absorbency, potentially non-removable, core component and a replaceable core component is first placed on the body of a wearer. The absorbent article is then placed in the higher absorbency configuration while or before the wearer is en route to a location to engage in water-related activities, such as a pool, lake, or water park. It is to be appreciated that the absorbent article may also be placed in the higher absorbency configuration before being placed on the wearer. While continuing to wear the absorbent article, the absorbent article is placed in the swim configuration. The wearer then exposes the absorbent article to water by engaging in water-related activities, such as sitting and/or playing in a swimming pool. During such time, the low absorbency core component may become saturated with water. The wearer then removes the absorbent article from exposure to water by discontinuing the water-related activity, for example, by exiting the swimming pool.

In a variation of the previously discussed method of use, the absorbent article may be placed in the higher absorbency configuration upon exiting the water to remove water from the absorbent article. More particularly, when placed in the higher absorbency configuration, the replaceable core component extracts water from the low absorbency core component. For example, upon exiting a pool, a dry replaceable core component can be inserted into the chassis and placed in capillary liquid communication with the low absorbency core component. The replaceable core component then extracts and absorbs water held in the low absorbency core component. The replaceable core component can then be removed from the chassis, resulting in a relatively dry swim pant. As such, a relatively dry swim pant may provide additional comfort to the wearer while engaging in activities away from the water. Such activities may include playing on a pool deck, taking a nap, eating lunch, etc. In addition, the removed water allows the low absorbency core components to better hold and store bodily exudates from the wearer.

In yet another variation of the method discussed above, the absorbent article may be placed in the higher absorbency configuration upon exiting the water to remove water from the absorbent article and to configure the absorbent article as a high absorbency diaper. For example as discussed above, upon exiting a pool, a dry replaceable core component can be inserted into the chassis and placed in capillary liquid communication with the low absorbency core component. The replaceable core component then extracts and absorbs water held in the low absorbency core component. The replaceable core component can remain in the chassis or can be removed and replaced with a replacement dry replaceable core component. As such, the relatively dry low absorbency core component in combination with the replaceable core component increase the absorbency of the diaper beyond the absorbency when placed in the swim configuration. The increased absorbency allows the diaper to absorb and retain greater amounts of bodily exudates and may reduce the chances of leakage while engaging in activities away from the water and/or while traveling to another destination, such as traveling home from a pool. From the higher absorbency configuration, the absorbent article can easily be reconverted to the swim configuration if the wearer desires to re-engage in water-related activities by simply removing the replaceable absorbent core component.

It is to be appreciated that the chassis of the disposable absorbent articles with replaceable core components described herein may be modified to include other characteristics. For example, the chassis of the absorbent articles may include a drain. In some configurations, when the absorbent article is placed in the swim configuration or the higher absorbency configuration, the drain is adapted to allow water to drain therethrough after engaging in water-related activities. In other configurations, the replaceable core component may be configured to selectively cover and/or block the drain when the absorbent article is placed in the higher absorbency configuration.

The above described disposable absorbent articles with replaceable core components may also be supplied and/or packaged to encourage use of these articles as swim pants in accordance with the above described methods of use. For example, the absorbent articles may be supplied as part of a kit in a package including one or more chassis, replaceable core components, instructions, and/or insertion tools if required. In another example, various components, such as the chassis, replaceable core components, and/or insertion tools may be supplied in packages with instructions for practicing the above described uses for swim pants. These components may also be configured with corresponding icons or other indicia that provide indications to the user that such items are adapted to work together as a swim pant. For example, the components and/or packages may include graphics with an aquatic theme to encourage usage of the components together as a swim pant and swim pant accessories.

It is to be appreciated that other variations of the above described methods for using and wearing absorbent articles as a swim pant are possible. In addition, it is to be appreciated that the order in which the steps are performed may vary from what has been described herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for using an article of commerce as a swim pant, the method comprising the steps of:
    wearing a disposable absorbent article comprising:
        a chassis;
        at least one absorbent core component disposed within the chassis;
        wherein the disposable absorbent article is selectively configured in a high absorbency configuration by placing a second absorbent core component in liquid communication with the at least one absorbent core component; and
        wherein the disposable absorbent article is selectively configured in a swim configuration by removing the second absorbent core component from liquid communication with the at least one absorbent core component; and
    engaging in a water-related activity with the disposable absorbent article in the swim configuration.

2. The method of claim 1, further comprising the step of:
    saturating the at least one absorbent core component with water.

3. The method of claim 2, further comprising the step of:
    extracting water from the at least one absorbent core component by selectively configuring the article in a high absorbency configuration by placing the second absorbent core component in liquid communication with the at least one absorbent core component.

4. The method of claim 3, further comprising the step of:
    reconfiguring the article in the swim configuration by removing the second absorbent core component from liquid communication with the at least one absorbent core component.

5. The method of claim 4, further comprising the step of:
    re-engaging in a water-related activity while wearing the disposable absorbent article in the swim configuration.

6. The method of claim 5, further comprising the steps of:
    reconfiguring the article in a high absorbency configuration by placing a replacement second absorbent core component in liquid communication with the at least one absorbent core component.

7. A method for using an article of commerce as a swim pant, the method comprising the steps of:
- wearing a diaper configurable between a high absorbency configuration and a swim configuration, the diaper comprising:
  - a chassis; and
  - a first absorbent core component disposed within the chassis;
  - wherein the diaper is selectively configured in the high absorbency configuration by placing a second absorbent core component in liquid communication with the first absorbent core component; and
  - wherein the diaper is selectively configured in the swim configuration by removing the second absorbent core component from liquid communication with the first absorbent core component; and
- selectively configuring the diaper between the high absorbency configuration and the swim configuration.

8. The method of claim 7, further comprising the steps of:
- engaging in a water-related activity with the diaper in the swim configuration; and
- saturating the first absorbent core component with water.

9. The method of claim 8, further comprising the step of:
- extracting water from the first absorbent core component by placing the diaper in the high absorbency configuration.

10. The method of claim 9, further comprising the step of:
- returning the diaper to the swim configuration.

11. The method of claim 10, further comprising the step of:
- re-engaging in a water-related activity while wearing the diaper.

12. The method of claim 11, further comprising the steps of:
- returning the diaper to the high absorbency configuration by placing a replacement second absorbent core component in liquid communication with the first absorbent core component.

* * * * *

UNITED STATES PATENT AND TRADEMARK OFFICE
CERTIFICATE OF CORRECTION

PATENT NO. : 7,824,386 B2  
APPLICATION NO. : 11/588134  
DATED : November 2, 2010  
INVENTOR(S) : LaVon et al.

It is certified that error appears in the above-identified patent and that said Letters Patent is hereby corrected as shown below:

<u>Column 6</u>

Line 17, delete "Bemardin" and insert --Bernardin--.

Line 18, delete "Bemardin" and insert --Bernardin--.

Line 33, delete "Bemardin" and insert --Bernardin--.

Line 45, delete "Homey" and insert --Horney--.

Signed and Sealed this  
Twenty-first Day of June, 2011

David J. Kappos  
*Director of the United States Patent and Trademark Office*